(12) United States Patent
Lin et al.

(10) Patent No.: US 12,122,809 B2
(45) Date of Patent: *Oct. 22, 2024

(54) IMMUNOMODULATORY PROTEIN FOR ALLEVIATION AND/OR TREATMENT OF CORONAVIRUS DISEASES

(71) Applicant: MYCOMAGIC BIOTECHNOLOGY CO., LTD, New Taipei (TW)

(72) Inventors: Tung-Yi Lin, Taipei (TW); Hsin Yeh, Taichung (TW); Zhi-Hu Lin, Taipei (TW)

(73) Assignee: MYCOMAGIC BIOTECHNOLOGY CO., LTD., New Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 18/153,973

(22) Filed: Jan. 12, 2023

(65) Prior Publication Data

US 2023/0220017 A1 Jul. 13, 2023

Related U.S. Application Data

(60) Provisional application No. 63/266,716, filed on Jan. 12, 2022.

(51) Int. Cl.
*C07K 14/375* (2006.01)
*A61K 38/00* (2006.01)

(52) U.S. Cl.
CPC ............ *C07K 14/375* (2013.01); *A61K 38/00* (2013.01)

(58) Field of Classification Search
CPC .............................. C07K 14/375; A61K 38/00
See application file for complete search history.

(56) References Cited

U.S. PATENT DOCUMENTS

2007/0207954 A1* 9/2007 Lin ..................... C07K 14/375
530/371
2011/0318429 A1* 12/2011 Ko ......................... A61P 35/04
424/649

FOREIGN PATENT DOCUMENTS

WO WO-2004092210 A2 * 10/2004 .......... A61K 39/0011
WO WO 2021/222240 * 11/2021 ............ A61K 31/495
WO WO 2022/195581 * 9/2022 ............. A61K 36/06

OTHER PUBLICATIONS

Jan et al., 2021, Identification of existing pharmaceuticals and herbal medicines as inhibitors of SARS-COV-2 infection, PNAS, 118(5): e2021579118 (8 pages).*
Li et al., 2021, N-Glycosylated Ganoderma lucidum immunomodulatory protein improved anti-inflammatory activity via inhibition of the p38 MAPK pathway, Food Funct, 12: 3393-3404.*
Rahman et al., 2021, Rationalization of Mushroom-Based Preventative and Therapeutic Approaches to COVID-19: Review, International Journal of Medicinal Mushrooms, 23(5): 1-11.*
Al-Jumaili, Miqdam M. Obaid et al. "The role of Ganoderma lucidum uptake on some hematological and immunological response in patients with coronavirus (COVID-19)." Sys. Rev. Pharm 11.8 (2020): 537-541.
Office Action issued in Taiwan patent application No. 112101453 on Jun. 27, 2023.
Shao, Ke-Di, et al. "Characterization of a novel fungal immunomodulatory protein, FIP-SJ75 shuffled from Ganoderma lucidum, Flammulina velutipes and Volvariella volvacea." Food and Agricultural Immunology 30.1 (2019): 1253-1270.
Cavalli, Giulio et al., "Interleukin-1 blockade with high-dose anakinra in patients with COVID-19, acute respiratory distress syndrome, and hyperinflammation: a retrospective cohort study," Lancet Rheumatology, (Jun. 2020), vol. 2, pp. e325-e331 (8 pages).
Chen, Chu, "COX-2's new role in inflammation," Nature Chemical Biology, (2010), vol. 6, pp. 401-402.
Cinelli, Maris A. et al., "Inducible Nitric Oxide Sunthase: Regulation, Structure, and Inhibition," Med Res Rev., (2020), vol. 40, No. 1, pp. 158-189.
Fajgenbaum, David C., M.D et al., "Cytokine Storm," New England Journal of Medicine, Dec. 3, 2020, vol. 383, Iss. 23, pp. 2255-2273.
Farooq, S. MBBS et al., "Post COVID-19 pulmonary fibrosis," Oxford University Press, (2021), downloaded from https://mc.manuscriptcentral.com/qim. 5 pages.
Gasparello, Jessica et al., "Sulforaphane inhibits the expression of interleukin-6 and interleukin-8 induced in bronchial epithelial IB3-1 cells by exposure to the SARS-CoV-2 Spike protein," Phytomedicine, (2021), vol. 87, pp. 1-8 (9 pages).
Herrera, Jeremy et al., "Extracellular matrix as a driver of progressive fibrosis," J. of Clinical Investigation, (2018), vol. 128, No. 1, pp. 45-53.
Hoffmann, Markus et al., "SARS-CoV-2 Cell Entry Depends on ACE2 and ATMPRSS2 and Is Blocked by a Clinically Proven Protease Inhibitor," Cell, Apr. 16, 2020, vol. 181, pp. 271-280.
Hsin I-Lun et al., "GMI, an Immunomodulatory Protein from Ganoderma microsporum, Potentiates Cisplatin-Induced Apoptosis via Autophagy in Lung Cancer Cells," Molecular Pharmaceutics, (2015), vol. 12, pp. 1534-1543.
Hsin, I-Lun et al., "GMI, an immunomodulatory protein from Ganoderma microsporum, induces autophagy in non-small cell lung cancer cells," Autophagy, (Aug. 2011), vol. 7, No. 8, pp. 873-882 (11 pages).
Hsu, Wei-Hung et al., "Effects of WSG, a polysaccharide from Ganoderma lucidum, on suppressing cell growth and mobility of lung cancer," International Journal of Biological Micromolecules, (2020), vol. 165, pp. 1604-1613.
Hu, Biying et al., "The cytokine storm and COVID-19," J of Med Virol, (Jun. 22, 2020), vol. 93, pp. 250-256.
Khan, Fasihul A. et al., "Systematic review and meta-analyisi of anakinra, sarilumab, siltuximab and tocilzumab for COVID-19," Thorax, Respiratory Infection, (2021), 0:1-13. doi: 10.1136/thoraxjnl-2020-215266.

(Continued)

*Primary Examiner* — Amber D Steele
(74) *Attorney, Agent, or Firm* — Prosyla Group PC

(57) ABSTRACT

The present disclosure relates to a method for alleviating and/or treating a coronavirus disease in a subject in need thereof, including administering an effective amount of *Ganoderma* immunomodulatory protein, a recombinant thereof or a fragment thereof to the subject.

15 Claims, 12 Drawing Sheets

Specification includes a Sequence Listing.

(56) References Cited

OTHER PUBLICATIONS

Kim, Jae Seok et al., "Immunopathogenesis and treatment of cytokine storm in COVID-19," Theranostics, 2021, col. 11, Issue 1, pp. 316-329.

Kino, Kohsuke et al., "Isolation and Characterization of a New Immunomodulatory Protein, Ling Zhi-8 (LZ-8), from Ganoderma lucidium," J. Biol. Chem., (Jan. 5, 1989), vol. 264, pp. 472-478.

Landi, Lorenza et al., "Blockage of interleukin-1 [beta] with canakinumab in patients with Covid-19," Scientific Reports, Nature Research, (2020), vol. 10, pp. 21775-783 (9 pages).

Li, Qi-Zhang et al., "Fungal immunomodulatory proteins: characteristic, potential antitumor activities and their molecular mechanisms," Drug Discovery Today, (Sep. 2018), vol. 00, No. 00, pp. 1-8.

Lin, Tung-Yi and Hsu, Hsien-Yeh, "Ling Zhi-8 reduces lung cancer mobility and metastasis through disruption of focal adhesion and induction of MDM2-mediated Slug degradation," Cancer Letters, (2016), vol. 375, pp. 340-348.

Lin, Tung-Yi et al., "Functional proteomic analysis reveals that fungal immunomodulatory protein reduced expressions of heat shock proteins correlates to apoptosis in lung cancer cells," Phytomedicine, (2021), vol. 80, pp. 1-10.

Lin, Zhi-Hu et al., "Water extract of medicinal ink (WEMI) attenuates lipopolysaccharide-induced NO production of Raw264.7 cells via downregulating JAK2/STAT3-mediated iNOS expression," J. of Ethnopharmacology, (2022), vol. 282, pp. 1-7.

Liu, Yusi et al., "Current Understanding of the Structure and Function of Fungal Immunomodulatory Proteins," Frontiers in Nutrition, (Aug. 2020), vol. 7, Art. 132, 17 pages.

Lu, Yong-Chen et al., "LPS/ATLR4 signal transduction pathway," Cytokine, (2008), vol. 42, pp. 145-151.

Matthay, Michael A. M.D., et al., "Biological Mechanisms of COVID-19 Acute Respiratory Distress Syndrome," Am J Respir Crit Care Med, Dec. 1, 2020, vol. 202, Iss. 11, 1489-1502.

Phillips, Jonathan E. et al., "Dry Powder and Nebulized Aerosol Inhalation of Pharmaceuticals Delivered to Mice Using a Nose-only Exposure System," J. of Visualized Experiments, (2017), vol. 122, e55454, 10 pages.

Richardson, Peter et al., "Baricitinib as potential treatment for 2019-nCoV acute respiratory disease," The Lancet, (Feb. 2020), vol. 395, pp. e30-e31 (3 pages). www.thelancet.com.

Sun, Jie et al., "Measurement of Nitric Oxide Production in Biological Systems by Using Griess Reaction Assay," Sensors, (2003), vol. 3, pp. 276-284.

Tay, Matthew Zirui et al., "The trinity of COVID-19: immunity, inflammation and intervention," Nature Reviews, Jun. 2020, vol. 20, pp. 363-374.

The Lancet, "Trials of anti-tumour necrosis factor therapy for COVID-19 are urgently needed," (May 2020), vol. 395, pp. 1407-1409 (4 pages). www.thelancet.com.

Vannucchi, Alessandro M. et al., "Compassionate use of JAK1/2 inhibitor ruxolitinib for severe COVID-19: a prospective observational study," Leukemia (2021), vol. 35, pp. 1121-1133.

Willis, Brigham C., et al., "Epithelial Origin of Myofibroblasts during Fibrosis in the Lung," Proc Am Thorac Soc, (2006), vol. 3, pp. 377-382.

Wu, Chaomin, MD et al., "Risk Factors Associated With Acute Respiratory Distress Syndrome and Death in Patients With Coronavirus Disease 2019 Pneumonia in Wuhan, China," JAMA Internal Medicine, Mar. 2020, 20 pages.

Yang, Lan et al., "The signal pathways and treatment of cytokine storm in COVID-19," Signal Transduction and Targeted Therapy, (2021), vol. 6, pp. 255-274 (20 pages).

Yang, Yang et al., "Traditional Chinese Medicine in the Treatment of Patients Infected with 2019-New Coronavirus (SARS-CoV-2): a Review and Perspective," Int. J. Biol., (2020), vol. 16, pp. 1708-1717.

Ye, Qing et al., "The pathogenesis and treatment of the 'Cytokine Storm' in COVID-19," Journal of Infection, (2020), vol. 80, pp. 607-613. (8 pages).

Zheng, Min et al., "TLR2 senses the SARS-COV-2 envelope protein to produce inflammatory cytokines," Nat Immunol., (2021), vol. 22, No. 7, pp. 829-838.

Zhou, Yu-Wen et al., "Therapeutic targets and interventional strategies in COVID-19: mechanisms and clinical studies," Signal Transduction and Targeted Therapy, Aug. 26, 2021, vol. 6, pp. 317 (25 pages). www.nature.com/sigtrans.

* cited by examiner

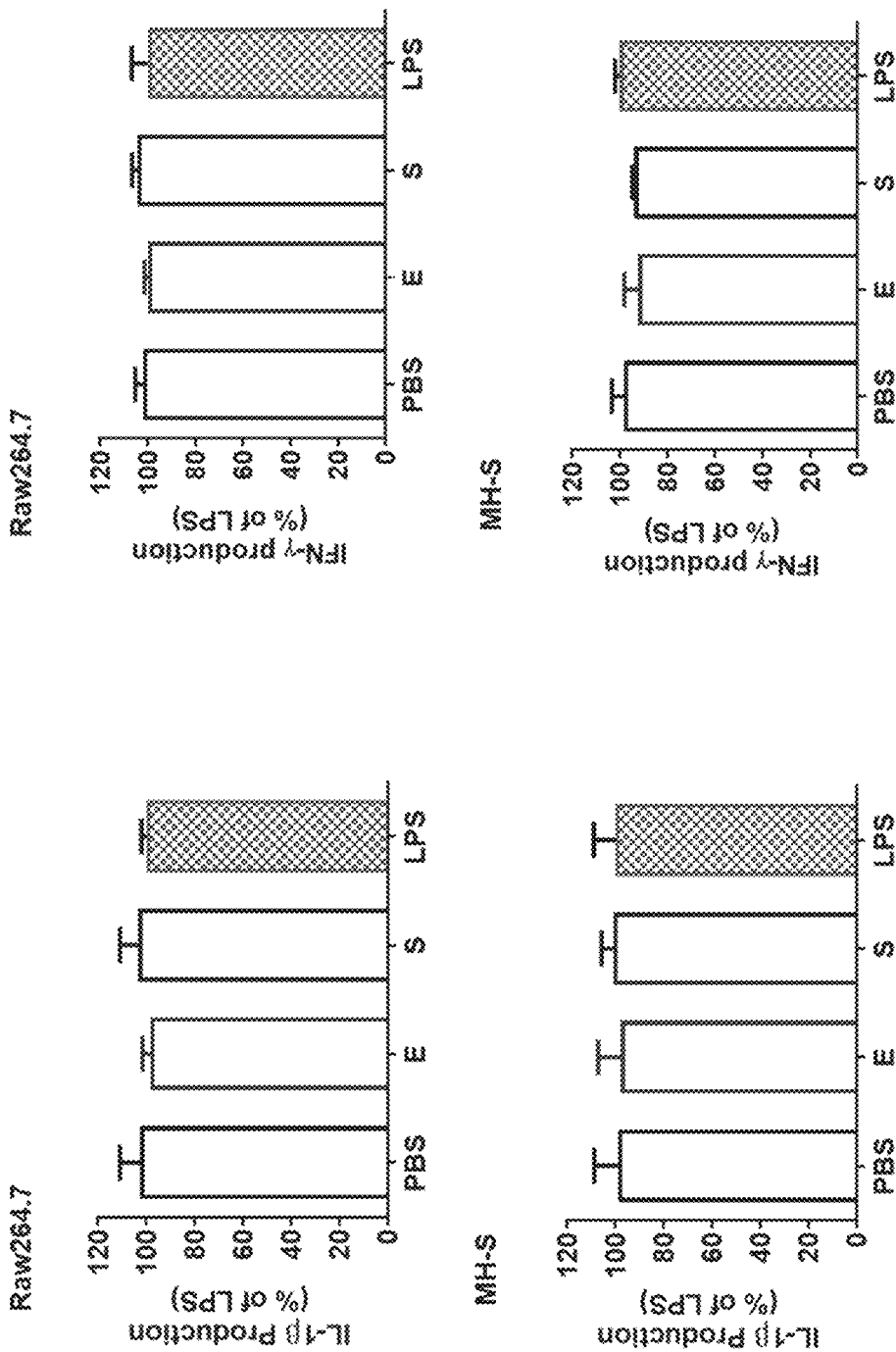

IMMUNOMODULATORY PROTEIN FOR ALLEVIATION AND/OR TREATMENT OF CORONAVIRUS DISEASES

RELATED APPLICATIONS

This application claims priority to U.S. Provisional Application Ser. No. 63/266,716, filed Jan. 12, 2022, the content of which is incorporated herein by reference in its entirety.

SEQUENCE LISTING

The instant application contains a Sequence Listing which is submitted electronically in .xml format and is hereby incorporated by reference in its entirety. The .xml copy, created on Jan. 12, 2023, is named "G4590-15600US_SeqListing_20230112.xml" and is 5 kilobytes in size.

FIELD OF THE INVENTION

The present disclosure relates to the field of inhibition and/or treatment of coronavirus (CoV) envelope protein-induced inflammation. Particularly, the present disclosure pertains to the use of an immunomodulatory protein from *Ganoderma* in treating coronavirus diseases.

BACKGROUND OF THE INVENTION

The pandemic coronavirus disease 2019 (COVID-19) that has swept the world since December 2019 is caused by the Severe Acute Respiratory Syndrome Coronavirus 2 (SARS-CoV-2). It is well known that SARS-CoV-2 infection depends on the interaction between a spike protein of SARS-CoV-2 and an angiotensin-converting enzyme 2 (ACE2) of host cells [1]. Once human cells or tissues are infected, SARS-CoV-2 will cause a series of reactions in the body, including virus production, initiating immune responses, and releasing many mediators to fight the infection. In clinical practice, severe COVID-19 induces systemic hyper-inflammation, known as cytokine storm, causing acute respiratory distress syndrome (ARDS), multiple organ failure and even death [2, 3]. Specifically, increasing evidence shows that COVID-19 induced ARDS in patients has high mortality rates compared to patients without ARDS-related symptoms [4, 5]. Therefore, an urgent clinical strategy is to develop a means of alleviating the cytokine storm in patients with COVID-19.

Cytokine storm is a clinical condition of uncontrolled hyper-inflammation caused by activated immune cells which overproduce various inflammatory cytokines [6]. Currently, many studies show that the high levels of pro-inflammatory cytokines such as tumor necrosis factor (TNF), interleukin (IL)-1, IL-6, IL-8 and IL-12, and chemokines such as interferon (INF) and monocyte chemoattractant protein-1 (MCP-1) create a cytokine storm in patients with severe COVID-19, causing damage to multiple organs or even death [2, 7, 8]. As such, blocking these inflammatory mediators may be a strategy for treating the severe COVID-19 patients.

Therefore, there is a need to develop a new therapeutic strategy against coronavirus diseases.

SUMMARY OF THE INVENTION

The present disclosure is based in part on the therapeutic measures of CoV diseases. It was surprisingly found that an immunomodulatory protein from *Ganoderma* can inhibit coronavirus envelope protein-induced inflammation and thus alleviate or treat coronavirus diseases such as Severe Acute Respiratory Syndrome Coronavirus Type 2 (SARS-CoV-2).

In one aspect, the present disclosure provides a method for inhibiting coronavirus-induced inflammation in a subject, comprising administering an effective amount of *Ganoderma* immunomodulatory protein, a recombinant thereof or a fragment thereof to the subject. Alternatively, the present disclosure provides *Ganoderma* immunomodulatory protein, a recombinant thereof or a fragment thereof for use in a method for inhibiting coronavirus-induced inflammation in a subject. In one embodiment, the method inhibits coronavirus-induced inflammation in macrophages and reduces collagen in lung cells. In one embodiment, the inflammation is induced by coronavirus protein. In a further embodiment, the inflammation is induced by coronavirus envelope (E) protein or coronavirus spike(S) protein.

In another aspect, the present disclosure provides a method for alleviating and/or treating coronavirus diseases in a subject, comprising administering a composition comprising an effective amount of *Ganoderma* immunomodulatory protein, a recombinant thereof or a fragment thereof to the subject. Alternatively, the present disclosure provides a composition comprising an effective amount of *Ganoderma* immunomodulatory protein, a recombinant thereof or a fragment thereof for use in a method for alleviating and/or treating coronavirus diseases in a subject. In one embodiment, the coronavirus diseases are alleviated and/or treated via inhibition of coronavirus-induced inflammation and reduction of collagen in lung cells. In one embodiment, the inflammation is induced by coronavirus protein. In a further embodiment, the inflammation is induced by coronavirus envelope (E) protein or coronavirus spike(S) protein.

In one embodiment, the *Ganoderma* immunomodulatory protein, a recombinant thereof or a fragment thereof is administered at a dose of about 1 µg/kg to about 100 µg/kg, preferably between about 1.5 µg/kg and about 90 µg/kg, about 1.5 µg/kg and about 80 µg/kg, about 1.5 µg/kg and about 70 µg/kg, about 1.5 µg/kg and about 60 µg/kg, about 1.5 µg/kg and about 50 µg/kg, about 1.5 µg/kg and about 40 µg/kg, about 1.5 µg/kg and about 30 µg/kg, about 1.5 µg/kg and about 20 µg/kg, or about 1.5 µg/kg and about 10 µg/kg. In one embodiment, the *Ganoderma* immunomodulatory protein, a recombinant thereof or a fragment thereof is administered at a dose selected from the group consisting of: about 1.0 µg/kg, about 1.5 µg/kg, about 2.0 µg/kg, about 2.5 µg/kg, about 3.0 µg/kg, about 3.5 µg/kg, about 4.0 µg/kg, about 4.5 µg/kg, about 5.0 µg/kg, about 5.5 µg/kg, about 6.0 µg/kg, about 6.5 µg/kg, about 7.0 µg/kg, about 7.5 µg/kg, about 8.0 µg/kg, about 8.5 µg/kg, about 9.0 µg/kg, about 9.5 µg/kg, about 10 µg/kg, about 15 µg/kg, about 20 µg/kg, about 25 µg/kg, about 30 µg/kg, about 35 µg/kg, about 40 µg/kg, about 45 µg/kg, about 50 µg/kg, about 55 µg/kg, about 60 µg/kg, about 65 µg/kg, about 70 µg/kg, about 75 µg/kg, about 80 µg/kg, about 85 µg/kg, about 90 µg/kg, about 95 µg/kg, and about 100 µg/kg.

In one embodiment, the inhibition of coronavirus-induced inflammation includes reduction in the blood NO level and/or in the level of at least one cytokine in blood and/or the lung selected from the group consisting of: IL-6, TNF-α, and IL-12.

In one embodiment, the *Ganoderma* immunomodulatory protein, a recombinant thereof or a fragment thereof described herein is derived from *Ganoderma lucidum, Ganoderma lucidum, Ganoderma tsugae, Ganoderma*

*microsporum* or *Ganoderma sinensis*. In a further embodiment, the *Ganoderma* immunomodulatory protein, a recombinant thereof or a fragment thereof is derived from *Ganoderma microsporum*.

In one embodiment, the *Ganoderma* immunomodulatory protein or a recombinant thereof described herein comprises an amino acid sequence of SEQ ID NO: 3. In one embodiment, the recombinant of *Ganoderma* immunomodulatory protein comprises an amino acid sequence of SEQ ID NO: 4. In one embodiment, the fragment of *Ganoderma* immunomodulatory protein comprises an amino acid sequence selected from the group consisting of SEQ ID NOs: 1 to 2.

The sequences of SEQ ID NOs: 1 to 4 are listed as follows.

```
                                           (SEQ ID NO: 1)
LAWNVK (SEQ ID NO: 2)
DLGVRPSYAV (SEQ ID NO: 3)
MSDTALIFTLAWNVKQLAFDYTPNWGRGRPSSFIDTVTFPTVLTDKAYTY

RVVVSGKDLGVRPSYAVESDGSQKINFLEYNSGYGIADTNTIQVYVIDPD

TGNNFIVAQWN (SEQ ID NO: 4)
EAEAEFMSDTALIFTLAWNVKQLAFDYTPNWGRGRPSSFIDTVTFPTVLT

DKAYTYRVVVSGKDLGVRPSYAVESDGSQKINFLEYNSGYGIADTNTIQV

YVIDPDTGNNFIVAQWNYLEQKLISEEDLNSAVDHHHHHH
```

In one embodiment, the *Ganoderma* immunomodulatory protein described herein consists of or essentially consists of an amino acid sequence selected from the group consisting of SEQ ID NOs: 1-4.

In some embodiments of the disclosure, the CoV described herein is alpha-CoV, beta-CoV, gamma-CoV, and delta-CoV2. In some embodiments, the CoV described herein includes, but is not limited to, SARS-CoV, MERS-CoV or SARS-CoV-2.

In one embodiment of the disclosure, the subject is vaccinated. In another embodiment, the subject is a severe CoV subject. In a further embodiment, the subject is a severe COVID-19 subject.

In one embodiment, the subject described herein has clinical improvement.

In one embodiment, the method described herein can shorten the time to recovery in subjects who were hospitalized with Covid-19, lower respiratory tract infection, and/or reduce mortality. In another embodiment, the method described herein can inhibit CoV-related (such as SARS-CoV-2-related) cytokine storm and fibrosis.

In some embodiments of the disclosure, the subject is administered one or more further therapeutic agents against CoV. In one embodiment, the one or more additional therapeutic agents is administered prior to or after administering the *Ganoderma* immunomodulatory protein, a recombinant thereof or a fragment thereof or is co-administered with the *Ganoderma* immunomodulatory protein, a recombinant thereof or a fragment thereof. In one embodiment, the one or more additional therapeutic agents is selected from the group consisting of: remdesivir, galidesivir, favilavir/avifavir, molnupiravir, AT-527, AT-301, BLD-2660, favipiravir, camostat, SLV213, emtrictabine/tenofivir, clevudine, dalcetrapib, boceprevir, ABX464, dexamethasone, hydrocortisone, convalescent plasma, gelsolin (Rhu-p65N), regdanvimab (Regkirova), ravulizumab (Ultomiris), VIR-7831/VIR-7832, BRII-196/BRII-198, COVI-AMG/COVI DROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab, otilimab, casirivimab/imdevimab (REGN-Cov2), MK-7110 (CD24Fc/SACCOVID), heparin, apixaban, tocilizumab (Actemra), sarilumab (Kevzara), apilimod dimesylate, DNL758, DC402234, PB1046, dapaglifozin, abivertinib, ATR-002, bemcentinib, acalabrutinib, baricitinib, tofacitinib, losmapimod, famotidine, ritonavir, niclosamide and diminazene.

In some embodiments of the disclosure, the *Ganoderma* immunomodulatory protein, a recombinant thereof or a fragment thereof is administered orally or by nasal nebulization. In one embodiment, the *Ganoderma* immunomodulatory protein, a recombinant thereof or a fragment thereof is administered by an inhaler to the respiratory tract for local or systemic treatment of the coronavirus disease. In one embodiment, the *Ganoderma* immunomodulatory protein, a recombinant thereof or a fragment thereof is in the form of aerosol with a size of 1 μm to 10 μm, preferably between 1.5 μm and 9 μm, between 2 μm and 8 μm, between 2.5 μm and 7 μm, or between 3 μm and 6 μm. In one further embodiment, the *Ganoderma* immunomodulatory protein, a recombinant thereof or a fragment thereof is in the form of aerosol with a size of 3 μm.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2A shows the NO production in macrophages determined by Griess assay after they were treated with SARS-CoV-2-E or S (1 μg/mL) for 24 h. FIG. 2B the IL-6 secretion of macrophages determined by ELISA after they were treated with SARS-CoV-2-E and S (1 μg/mL) for 24 h. LPS (lipopolysaccharide; 100 ng/mL) was the positive control. Each E or S-treated group was normalized against control (LPS alone treatment) group. The data were representative of three separate experiments and were presented as the mean±SDs; the error bars indicated SD. Significant differences were shown (*P<0.05 and *** P<0.001, compared with the control/CTL group). Non-significant differences were shown (N.S.) compared with the control group.

FIGS. 3A-3D show the effects of SARS-CoV-2 subunits on stimulating inflammatory responses of macrophages. FIGS. 3A-3D respectively show the production of TNF-α (FIG. 3A), IL-12 (FIG. 3B), IL-1β (FIG. 3C), and IFN-γ (FIG. 3D) in macrophages determined by ELISA after they were treated with SARS-CoV-2-E and S (1 μg/mL) for 24 h. LPS (lipopolysaccharide; 100 ng/mL) was the positive control. Each E or S-treated group was normalized against the control (LPS alone treatment) group. The data were representative of three separate experiments and were presented as the mean±SDs; the error bars indicated SD. Significant differences were shown (*** P<0.001, compared with the control/PBS group).

FIG. 4A shows the NO production in the macrophages that were stimulated with SARS-CoV-2-E or S (1 µg/mL) in the presence or absence of GMI (0.6 µM) for 24 h determined by Griess assay. FIGS. 4B-4D respectively show the production of IL-6 (FIG. 4B), TNF-α (FIG. 4C), and IL-12 (FIG. 4D) in the macrophages that were stimulated with SARS-CoV-2-E or S (1 µg/mL) in the presence or absence of GMI (0.6 µM) for 24 h determined by ELISA. LPS (lipopolysaccharide; 100 ng/ml) was the positive control. Each GMI-treated group was normalized against the control (LPS alone treatment) group. The data were representative of three separate experiments and were presented as the mean±SDs; the error bars indicated SD. Significant differences were shown (*** P<0.001, compared with the control group).

FIG. 5A shows the NO production in the macrophages that were stimulated with SARS-CoV-2-E or S (1 µg/mL) in the presence or absence of GMI (0-1.2 µM) for 24 h determined by Griess assay. FIGS. 5B-5D respectively show the production of IL-6 (FIG. 5B), TNF-α (FIG. 5C), and IL-12 (FIG. 5D) in the macrophages that were stimulated with SARS-CoV-2-E or S (1 µg/mL) in the presence or absence of GMI (0-1.2 µM) for 24 h determined by ELISA. LPS (lipopolysaccharide; 100 ng/ml) was the positive control. Each GMI-treated group was normalized against the control (LPS alone treatment) group. The data were representative of three separate experiments and were presented as the mean±SDs; the error bars indicated SD. Significant differences were shown (*P<0.05 and *** P<0.001, compared with the control group).

FIGS. 6A and 6B respectively show the expression of the iNOS (FIG. 6A) protein and the COX-2 protein (FIG. 6B) in macrophages that were treated with GMI (0.6 µM) for 3 h followed by stimulation with SARS-CoV-2-E (1 µg/mL) for another 24 h determined by Western blot in which Actin was used as the internal control.

FIG. 7A shows viability of PMA-induced THP-1 cells treated with GMI (0-1.2 µM) for 24 h determined by MTT assay. FIG. 7B shows viability of PMA-induced THP-1 cells treated with GMI (0-1.2 µM) and SARS-CoV-2-E (1 µg/mL) for 24 h determined by MTT assay. FIG. 7C shows the IL-6 production in PMA-induced THP-1 cells treated with GMI (0-1.2 µM) and SARS-CoV-2-E (1 µg/mL) for 24 h determined by ELISA. The data were representative of three separate experiments and were presented as the mean±SDs; the error bars indicated SD. Significant differences were shown (** P<0.01, compared with the control group).

FIG. 9A shows the scheme for mice receiving GMI (100 µg/mL) in the presence or absence of SARS-CoV-2-E (20 µg/mL) by the inhalation method. FIGS. 9B and 9C respectively show the IL-6 production in the lung tissue (FIG. 9B) and the blood serum (FIG. 9C) after exposure to GMI and/or SARS-CoV-2-E for 6 h or 24 h. The data were representative of three separate experiments and were presented as the mean±SDs; the error bars indicated SD. Significant differences were shown (*P<0.05,  P<0.01, and * P<0.001, compared with the control group; #P<0.05, and ## #P<0.001, compared with the SARS-CoV-2 individual treatment group).

DETAILED DESCRIPTION OF THE INVENTION

Figure 1B:
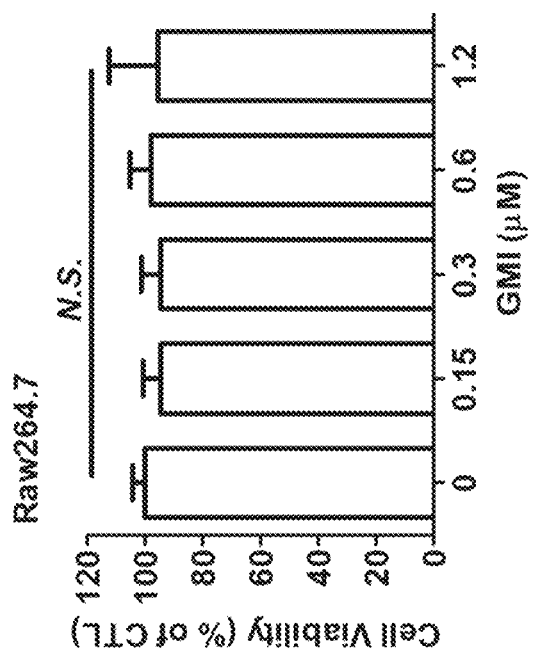
FIGS. 1A and 1B show the effects of GMI on viability of macrophages Raw264.7 (FIG. 1A) and MH-S cells (FIG. 1B). The values represented the means±SD. Non-significant differences were shown (N.S.) compared with the control group.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated for reference.

In this application, the use of the singular includes the plural, the article "a" or "an" means "at least one," and the use of "or" means "and/or," unless specifically stated otherwise.

The term "preventing" or "prevention" is recognized in the art, and when used in relation to a condition, it includes administering an agent to reduce the frequency or severity of or to delay the onset of symptoms of a medical condition in a subject, relative to a subject which does not receive the agent.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, "treating" and "ameliorating" are used interchangeably. These terms refer to an approach for obtaining beneficial or desired results including, but not limited to, therapeutic benefit and/or a prophylactic benefit. Therapeutic benefit pertains to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, "effective amount" means an amount of an agent to be delivered (e.g., drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

As used herein, "subject" refers to either a human or non-human animal.

The term "coronavirus" or "CoV" refers to any virus of the coronavirus family, including, but not limited to, SARS-CoV-2, MERS-CoV, and SARS-CoV. SARS-CoV-2 refers to the newly-emerged coronavirus which is rapidly spreading to other areas of the globe. It binds via the viral spike protein to the human host cell receptor angiotensin-converting enzyme 2 (ACE2). The spike protein also binds to and is cleaved by TMPRSS2, which activates the spike protein for membrane fusion of the virus.

The term "coronavirus infection" or "CoV infection," as used herein, refers to infection with a coronavirus such as SARS-CoV-2, MERS-CoV, or SARS-CoV. The term includes coronavirus respiratory tract infections, often in the lower respiratory tract. Symptoms can include high fever, dry cough, shortness of breath, pneumonia, gastro-intestinal symptoms such as diarrhea, organ failure (kidney failure and renal dysfunction), septic shock, and death in severe cases.

Currently, traditional anti-inflammatory drug glucocorticoid is commonly used to treat patients with SARS-CoV-2 infection because it can inhibit the NF-κB signals and thereby reduce the production of inflammatory factors [9]. In addition, using the cytokine or cytokine receptor antagonists may offer clinical benefits. For example, IL-1 signaling blockade by canakinumab and anakinra improved respiratory function in COVID-19 patients with ARDS [10, 11]. Siltuximab, sarilumab and tocilizumab targeted on IL-6 signaling may reduce severity and mortality in severe COVID-19 patients [12]. Etanercept blocks TNF-α cassette for reducing excessive cytokine release and hyperinflammation [13]. Moreover, blockade of cytokines-mediated downstream JAK/STAT signaling using baricitinib and ruxolitinib may be a promising strategy for improving an inflammatory condition in severe COVID-19 patients [14, 15]. However, there are still no suitable drugs in clinical practice. Development of a safe and effective drug to control SARS-CoV-2-induced cytokine storm and balance the immune responses in clinical practice is a quite an issue. Notably, repurposing herb derivatives to reduce inflammatory molecules may be used to improve the cytokine storm caused by SARS-CoV-2 [16].

The present disclosure surprisingly found that an immunomodulatory protein from *Ganoderma* can inhibit coronavirus-induced inflammation and thus alleviate or treat coronavirus diseases such as Severe Acute Respiratory Syndrome Coronavirus Type 2 (SARS-CoV-2). Accordingly, the present disclosure provides a method for inhibiting coronavirus-induced inflammation in a subject, comprising administering an effective amount of *Ganoderma* immunomodulatory protein, a recombinant thereof or a fragment thereof to the subject. Also, the present disclosure provides a method for alleviating and/or treating coronavirus diseases in a subject, comprising administering to the subject a composition comprising an effective amount of *Ganoderma* immunomodulatory protein, a recombinant thereof or a fragment thereof.

Fungal immunomodulatory proteins (FIPs) are a group of proteins found in fungi, which are extensively studied for their immunomodulatory activity, including activation of immune cells, leading to immune-mediated anti-allergic, anti-inflammatory, and anti-tumor effects. *Ganoderma* immunomodulatory protein is one kind of FIP derived from *Ganoderma*.

Since the first fungal protein was isolated from mushroom *Ganoderma lucidum* mycelium in 1989 [17], many new fungal proteins have been discovered. These identified fungal proteins have highly conserved amino acid sequences and structures, and have been proven to have the effect of regulating immune cells, so they are called fungal immunomodulatory proteins (FIPs) [18, 19]. Increasing evidence shows that FIPs exhibit various pharmacological functions such as anti-inflammation and anti-tumor, so they are considered to have a high potential for development as novel drugs [19].

The preparation of the *Ganoderma* immunomodulatory protein or the recombinant or fragment thereof has been described in U.S. Pat. No. 7,601,808. Particularly, the *Ganoderma* immunomodulatory protein is referred to as GMI; the recombinant of *Ganoderma* immunomodulatory protein is referred to as reGMI; and the fragment of *Ganoderma* immunomodulatory protein is referred to as SEQ ID NOs: 2 and 3 in U.S. Pat. No. 7,601,808. Some studies have been focusing on investigating the effects of GMI on anti-cancer activity but not on immunomodulatory functions because GMI suppresses tumor progression via induction of autophagy [20, 21].

In one embodiment of the present disclosure, the *Ganoderma* immunomodulatory protein or the recombinant or fragment thereof (such as GMI) is used to inhibit coronavirus envelope protein-induced inflammation, thus alleviating and/or treating coronavirus diseases in a subject. The present disclosure firstly explores the anti-inflammatory effects and potential mechanisms of *Ganoderma* immunomodulatory protein or the recombinant or fragment thereof (such as GMI) in CoV diseases. Moreover, it is found that SARS-CoV-2 envelop (E) protein but not spike(S) protein dramatically induced an inflammatory process in macrophages Raw264.7 and MH-S cells. GMI shows a strong inhibitory effect under SARS-CoV-2-E-induced pro-inflammatory mediators, including NO, TNF-α, IL-6, and IL-12. GMI reduces intracellular inflammatory molecules, such as iNOS and COX-2. In addition, GMI reduces collagen in lung cells. It is suggested that GMI can be employed as an agent to alleviate SARS-CoV-2-induced cytokine storm and fibrosis.

The immunomodulatory protein or a recombination thereof of the invention can be administered to a patient either alone or in pharmaceutical compositions where it is mixed with suitable carriers and excipients. The immunomodulatory protein, recombination thereof or composition of the invention can be administered parenterally, such as by nasal nebulization, intravenous injection or infusion, intraperitoneal injection, subcutaneous injection, or intramuscular injection. The immunomodulatory protein, recombination thereof or composition can be administered orally through appropriate formulation with carriers and excipients to form tablets, pills, capsules, liquids, gels, syrups, slurries, suspensions and the like. The immunomodulatory protein, recombination thereof or composition can be administered topically, such as by nasal nebulization. The immunomodulatory protein, recombination thereof or composition can be administered by inhaler to the respiratory tract for local or systemic treatment of CoV diseases.

The *Ganoderma* immunomodulatory protein, a recombinant thereof or a fragment thereof is administered at a dose of about 1 µg/kg to about 100 µg/kg. The dosage of the immunomodulatory protein, recombination thereof or composition suitable for use according to the present invention can be determined by those skilled in the art on the basis of the disclosure herein. The medicament will contain an effective dosage (depending upon the route of administration and pharmacokinetics of the active agent) of suitable pharmaceutical carriers and excipients suitable for the particular route of administration of the formulation (i.e., oral, parenteral, topical or by inhalation). The immunomodulatory protein or a recombination thereof is mixed into the pharmaceutical composition by means of mixing, dissolving, granulating, dragee-making, emulsifying, encapsulating, entrapping or lyophilizing processes. The pharmaceutical compositions for parenteral administration include aqueous solutions of the inventive polypeptide in water-soluble form. Additionally, suspensions of the inventive polypeptide may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

The following examples are provided to aid those skilled in the art in practicing the present disclosure.

EXAMPLE

Materials and Methods

Materials

GMI (with the amino acid sequence of SEQ ID NO: 4), dissolved in sterilized PBS, was gifted from MycoMagic Biotechnology Co., Ltd. (New Taipei, Taiwan). LPS (*E. coli* O55: B5) was purchased from Sigma-Aldrich. Phorbol 12-myristate 13-acetate (PMA; P-1039-1 MG) was purchased from AGScientific. SARS-CoV-2-E (NBP2-90986) was purchased from Novus Biologicals (CO, USA). SARS-CoV-2-S(SPN-C52H9) were purchased from ACROBiosystems (DE, USA).

Cell Lines

Raw264.7 (murine macrophages), MH-S(mouse alveolar macrophages), WI-38 VA-13 subline 2RA (WI38-2RA; lung fibroblast), MRC-5 (lung fibroblast), and THP-1 (human monocyte) cells were purchased from the Bioresource Collection and Research Center (BCRC, Hsinchu, Taiwan). Raw264.7 cells were maintained in Dulbecco's modified Eagle's medium (DMEM, GIBCO-Life Technologies) supplemented with 5% heat-inactivated fetal bovine serum (FBS, HyClone, Marlborough, MA), 100 units/mL of penicillin/streptomycin (Biological Industries, Cromwell, CT), and 3.7 g/L of $NaHCO_3$. MH-S cells were maintained in Roswell Park Memorial Institute (RPMI) 1640 medium (GIBCO-Life Technologies) with 2 mM L-glutamine adjusted to contain 1.5 g/L $NaHCO_3$, 4.5 g/L glucose, 10 mM HEPES and 1.0 mM sodium pyruvate and supplemented with 10% heat-inactivated FBS. WI38-2RA and MRC-5 cells were cultured in Eagle's Minimum essential medium (MEM, GIBCO-Life Technologies) with 10% FBS, 2 mM L-glutamine, 0.1 mM non-essential amino acids, and 1.0 mM sodium pyruvate and 1.5 g/L of $NaHCO_3$. THP-1 cells were maintained in Roswell Park Memorial Institute (RPMI) 1640 medium (CORNING, 10-040-CV) with 2 mM L-glutamine, 1× non-essential amino acid, 100 units/m penicillin, 0.1 mg/mL streptomycin, and 1.0 mM sodium pyruvate and supplemented with 10% heat-inactivated FBS. All of the adherent cells were detached by incubation with trypsin-EDTA (Invitrogen, Co., Carlsbad, CA). The cells were cultured in a 5% $CO_2$ atmosphere at 37° C.

Cell Viability Assay

Cells (5× $10^4$ cells) were seeded into 12-well plates and incubated for 12 h to analyze the cytotoxic effects of GMI. Cells were stimulated with LPS (100 ng/ml), SARS-CoV-2-E (1 µg/mL) or SARS-CoV-2-S(1 µg/mL) in the presence or absence of different concentrations of GMI (0-1.2 µM) for 24 h. After incubation, the 3-(4,5-dimethylthiazole-2-yl)-2,5-diphenyl tetrazolium bromide (MTT) dye was added to each well and incubated for 4 h. The cell viability was measured as previously described [22].

NO Production Assay

Cells (1×$10^5$ cells/well in 96-well for 24 h incubation) were stimulated with LPS (100 ng/mL), SARS-CoV-2-E (1 µg/mL) or SARS-CoV-2-S(1 µg/mL) in the presence or absence of GMI (0-1.2 µM) for 24 h simultaneously. Nitric oxide (NO) production was measured by Griess assay as in the previous study [23, 24]. Individual LPS-induced NO production was designated as 100% for each experiment.

Enzyme-Linked Immunosorbent Assay (ELISA) for Cytokines

Cells (5×$10^5$ cells in 24-well plates) were treated with various concentrations of GMI (0-1.2 µM) and vehicle (PBS) for 30 min, followed by LPS (100 ng/mL), SARS-CoV-2-E (1 µg/mL) or SARS-CoV-2-S(1 µg/mL) for 24 h. The levels of TNF-α, IL-6, IL-8, IL-12 and IFN-γ in the cultured medium of macrophages and lung epithelial cells were measured using an ELISA kit (BioLegend, San Diego, CA, USA) according to the manufacturer's instructions. A series of dilutions of various cytokines (ranging m 0 to 1000 pg/mL) were used as standard curves for each experiment. Data were collected by detecting A450 nm and A550 nm (reference absorbance) using a TECAN Sunrise™ ELISA Reader (Tecan Group Ltd., Männedorf, Switzerland). Individual LPS-induced production of cytokines was designated as 100% for each experiment.

Western Blot Assay

Cells (5×$10^5$ cells) were seeded in the 6-cm cell culture dishes for 24 h. Cells then were treated with LPS (100 ng/mL) or SARS-CoV-2-E (1 µg/mL), followed by GMI (0, 0.3 and 0.6 µM) for 24 h. After the treatment, cells were harvested and rinsed with cold PBS containing 1% $Na_3VO_4$ and lysed using the specific lysis buffer with protease inhibitor [25]. The cell lysates were collected by centrifugation for 13,000 xg for 10 min at 4° C. Cell lysates (30 µg) were separated on 10% SDS-PAGE and the indicated molecules were detected by western blot analysis as in the previous study [26]. Antibodies against COX-2, iNOS and tubulin were purchased from Genetex.

Animal Model

The male C57BL/6 mice (6-8 weeks) were used for in vivo study and purchased from National Laboratory Animal Center (NLAC, Taipei, Taiwan). Mice were isolated for at least 1 week before experimental manipulations and were approved by NYCU Institutional Animal Care and Use Committee (IACUC Approval NO: 1101212). GMI (100 µg) and E protein (20 µg) were dissolved in physiologic saline (1 mL). The mice were divided into 6 h and 24 h exposure groups exposed with PBS, GMI (100 µg/mL), or E protein (20 µg/mL) for 30 min. Nebulizer (Aerogen AG-AP1000, Aerogen Ltd. Galway, Ireland) administered GMI and E protein to the mouse at a flow rate of 0.25 ml/min. The mice were gently put in a 2.8 L cage and exposed to the GMI and E protein aerosol for 30 minutes. After exposure, the mice were sacrificed and the lung tissues and serum were harvested and stored at −80° C. To calculate the deposited doses of GMI, the following equation was used:

$$\text{Deposited Dose} \left(\frac{\mu g}{kg}\right) = \frac{\text{Concentration} \left(\frac{\mu g}{L}\right) \times \text{Minute Volume} \left(\frac{L}{min}\right) \times IF \times DF}{\text{Body Weight (kg)}} \text{[36]}.$$

The concentration of GMI in the air is 100 µg/2.8 L cage volume and E protein in the air is 20 µg/2.8 L cage volume. The respiratory minute volume was calculated as 0.021 L/min in mice. When there are no non-respirable particles in the aerosol, the inhalable fraction (IF) is 1, the deposition fraction (DF) is 0.055 which is related to the aperture of the nebulizer (3 µm), and the average body weight of the mice is 0.02 kg. The deposited doses of GMI for the 30 min exposure were 61.875 µg/kg, and the deposited doses of E protein for the 30 min exposure were 12.375 µg/kg.

On the other hand, the GMI dose for a human with a body weight of 60 kg can be converted from the aforementioned deposited dose for the mice with a body weight of 0.02 kg by the following equation [36]:

$$GMI \text{ Dose (human)} = GMI \text{ Deposited Dose (mice)} \times \left(\frac{\text{Body weight (human)}}{\text{Body weight (mice)}}\right)^{(1-b)},$$

in which b refers to the allometric exponent for the allometric approach to predicting a human dose from an available mouse dose. The commonly-used allometric exponent b for predicting human drug doses is 0.67. Given the GMI deposited dose of 61.875 µg/kg for mice, the GMI dose for a human with a body weight of 60 kg is 4.406 µg/kg.

Statistical Analysis

All data are expressed as mean±SD of more than three times independent experiments. Statistical differences between each experimental group were examined by t-test analyses using GraphPad Prism8. Statistical significance was set at *$P<0.05$.

Example 1 Effects of GMI on Viability of Macrophages Raw264.7 and MH-S Cells

Figure 1A:
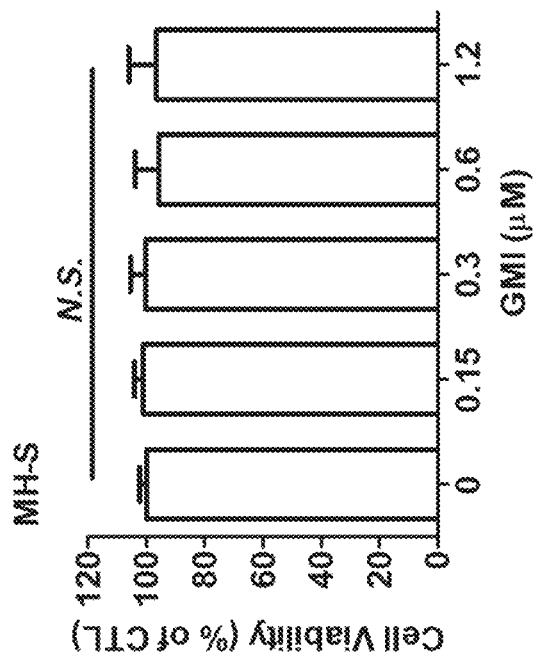

GMI is a kind of fungal immunomodulatory protein. We therefore hypothesized that GMI may play a pivotal role in modulating SARS-CoV-2-induced cytokine storm. It is well known that immune or epithelial cells could secret inflammatory factors after SARS-CoV-2 infection, consequently causing tissue damage and cytokine storm [27]. To explore the role of GMI on inflammation, we initially examined whether GMI affects cell viability of macrophages. Macrophages Raw264.7 and MH-S cells were chosen to determine the cytotoxic effect of GMI. MTT assay was performed to analyze the cell survival of Raw264.7 and MH-S cells after being treated with GMI for 24 h. As shown in FIGS. 1A-B, we found that GMI did not affect cell viability of Raw264.7 and MH-S cells at 0.15-1.2 µM, suggesting that GMI had no cytotoxicity for macrophages.

Figure 2A:
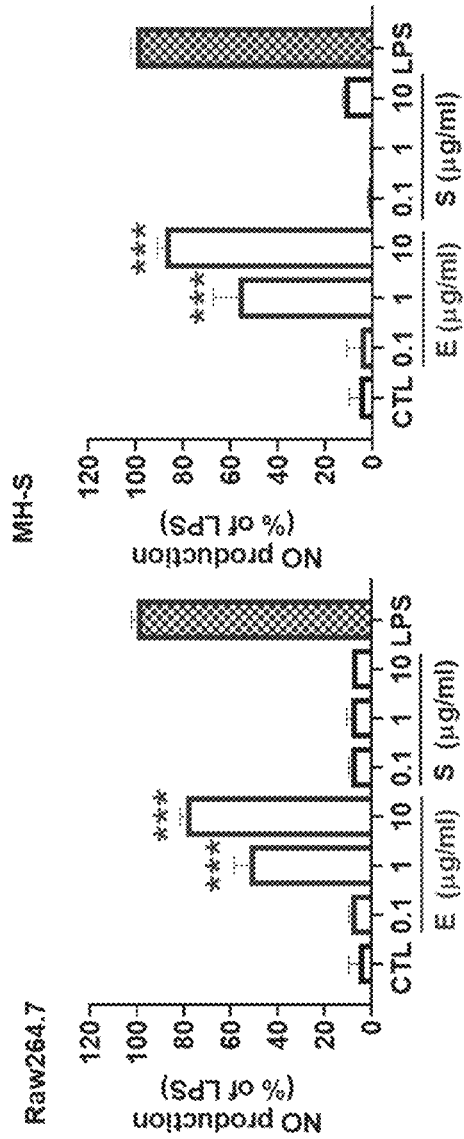
FIGS. 2A and 2B show the effects of SARS-CoV-2 subunits on stimulating inflammatory responses of macrophages.
Figure 2B:
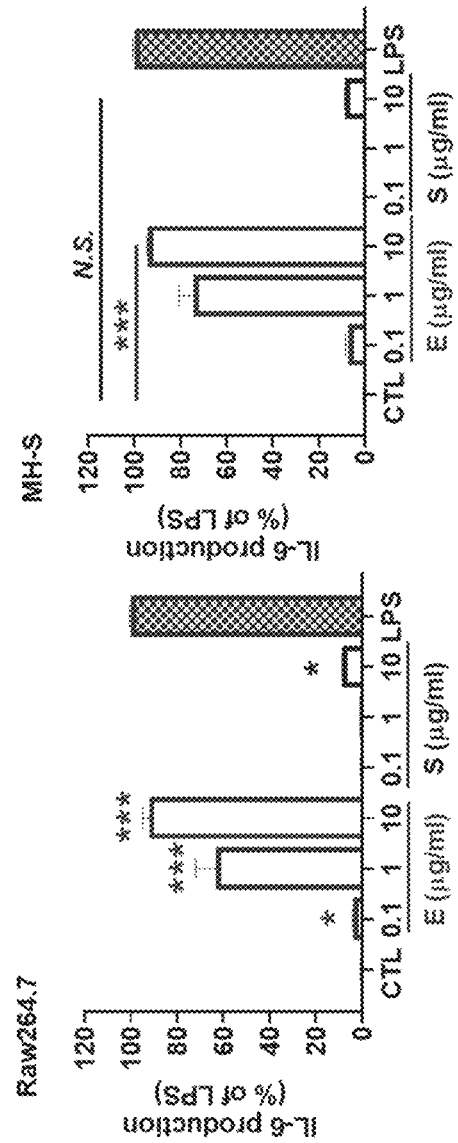
Figures 3A, 3B:
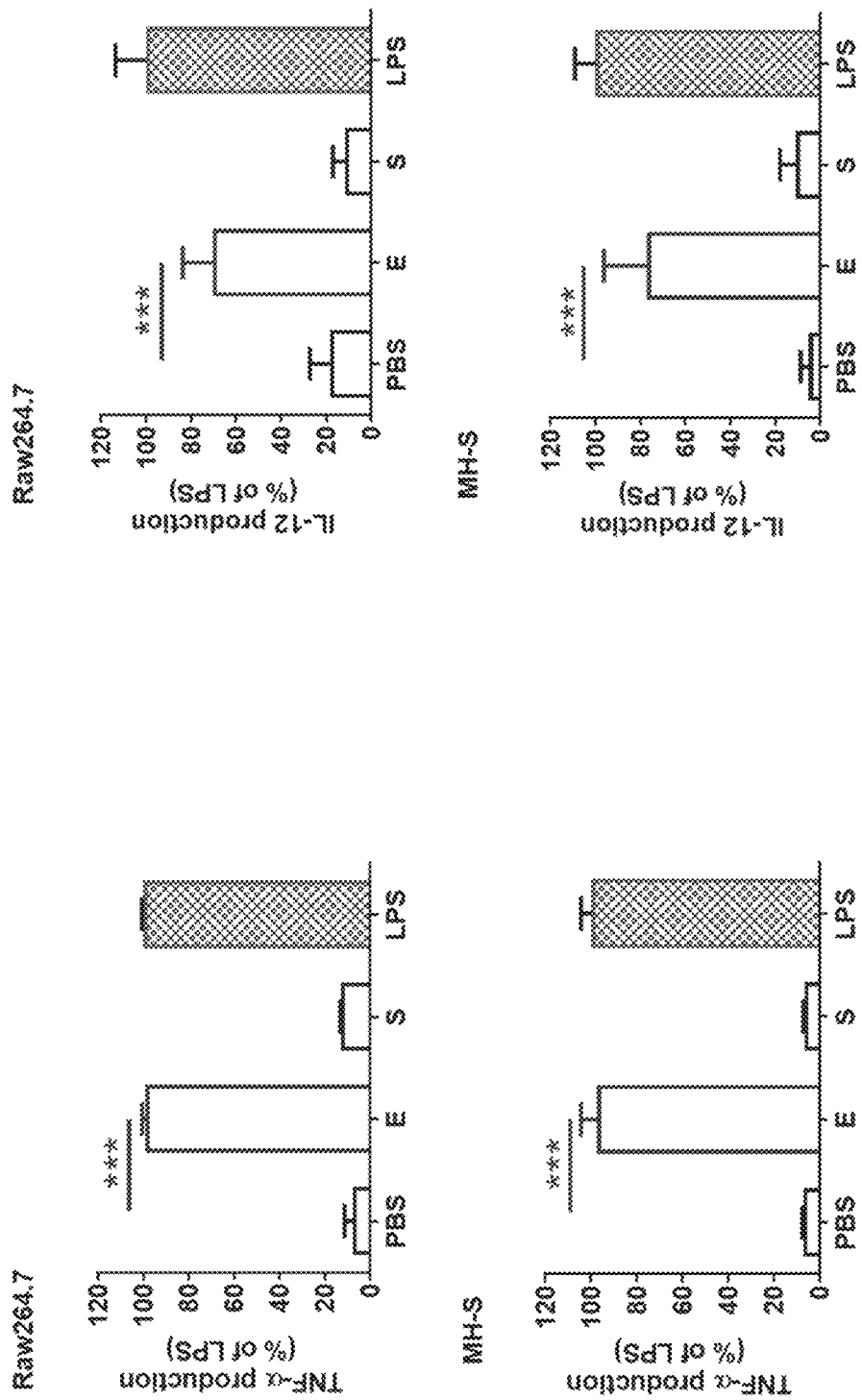

Example 2 Effects of SARS-CoV-2 Subunits on Stimulating Inflammatory Responses of Macrophages Previously, some studies show that SARS-CoV-2 subunits could induce inflammatory cytokines such as IL-6 and TNF-α [28, 29]. We thus examined whether SARS-CoV-2 subunits (SARS-CoV-2-E and SARS-CoV-2-S) induced inflammatory responses in RAW264.7 and MH-S cells. Generally, macrophages release nitric oxide (NO) and cytokines during LPS-stimulated acute inflammation [30]. Herein, LPS was used as the positive control. First, we examined whether SARS-CoV-2-E and SARS-CoV-2-S could induce NO in macrophages and found that SARS-CoV-2-E but not SARS-CoV-2-S dramatically increased the production of NO in a concentration-dependent manner (FIG. 2A). Also, SARS-CoV-2-E significantly induced IL-6 levels in both macrophages RAW264.7 and MH-S cells (FIG. 2B). In parallel, SARS-CoV-2-E could induce TNF-α and IL-12 (FIGS. 3A-B), whereas IL-1β and INF-γ were not induced by SARS-CoV-2-E and S (FIGS. 3C-D). These findings suggest that SARS-CoV-2-E may play a pivotal role in triggering the primary immune responses after SARS-CoV-2 infection.

Figures 4A, 4B:
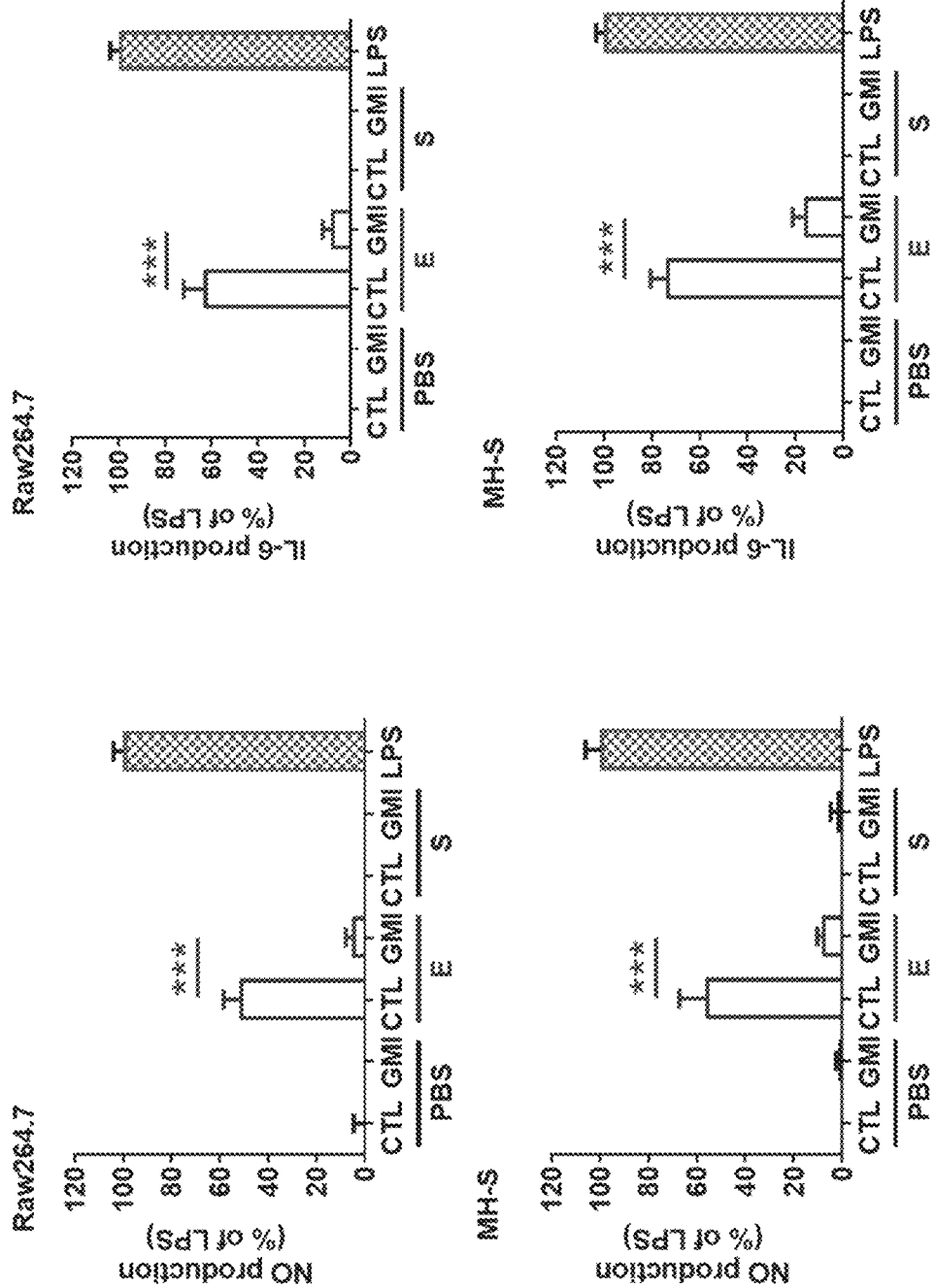
FIG. 4A-4D show effects of GMI on inhibiting SARS-CoV-2-E-induced inflammation of macrophages.
Figures 4C, 4D:
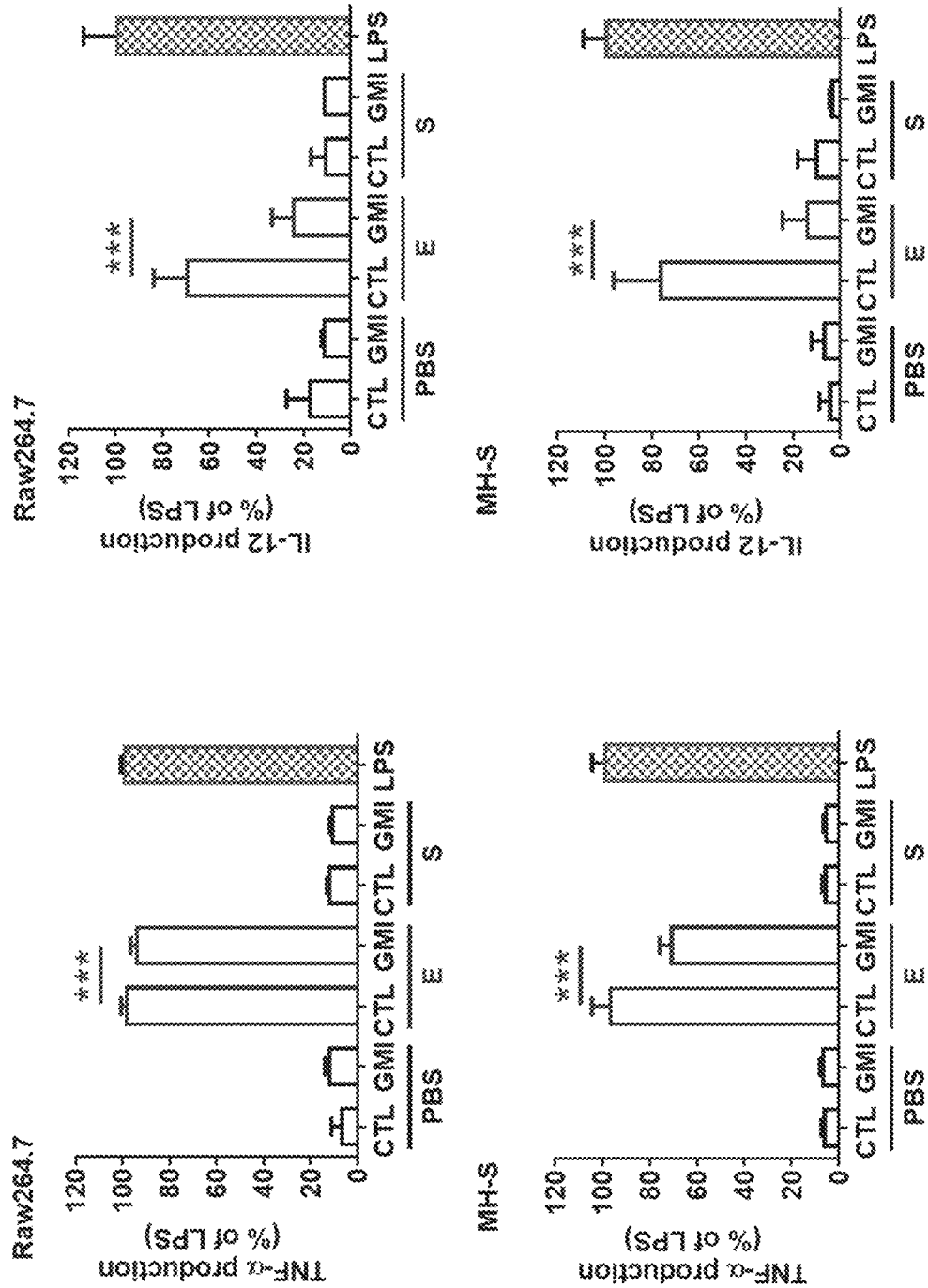
Figures 5A, 5B:
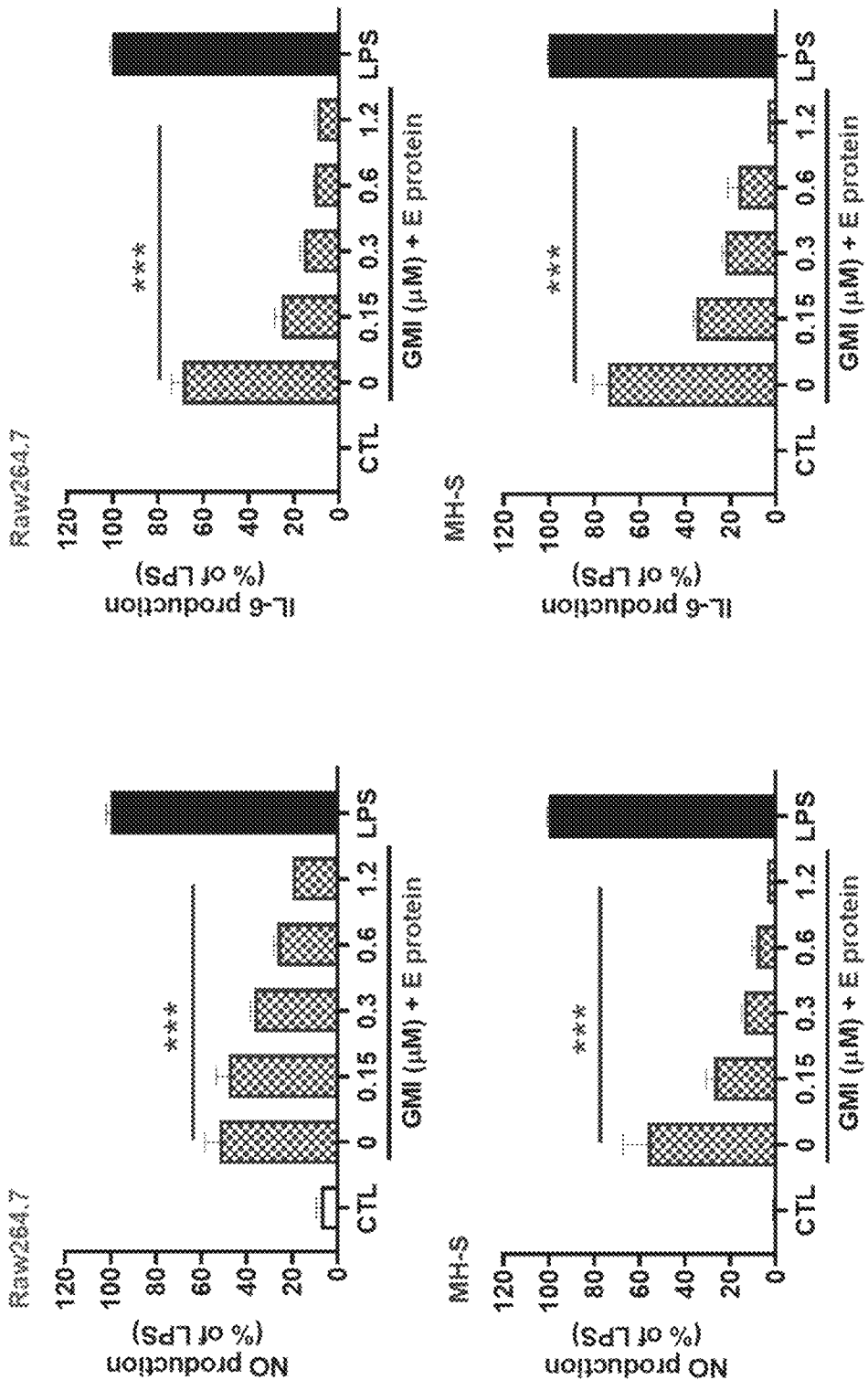
FIGS. 5A-5D show effects of GMI on inhibiting SARS-CoV-2-E-induced inflammation of macrophages in a concentration-dependent manner.
Figures 5C, 5D:
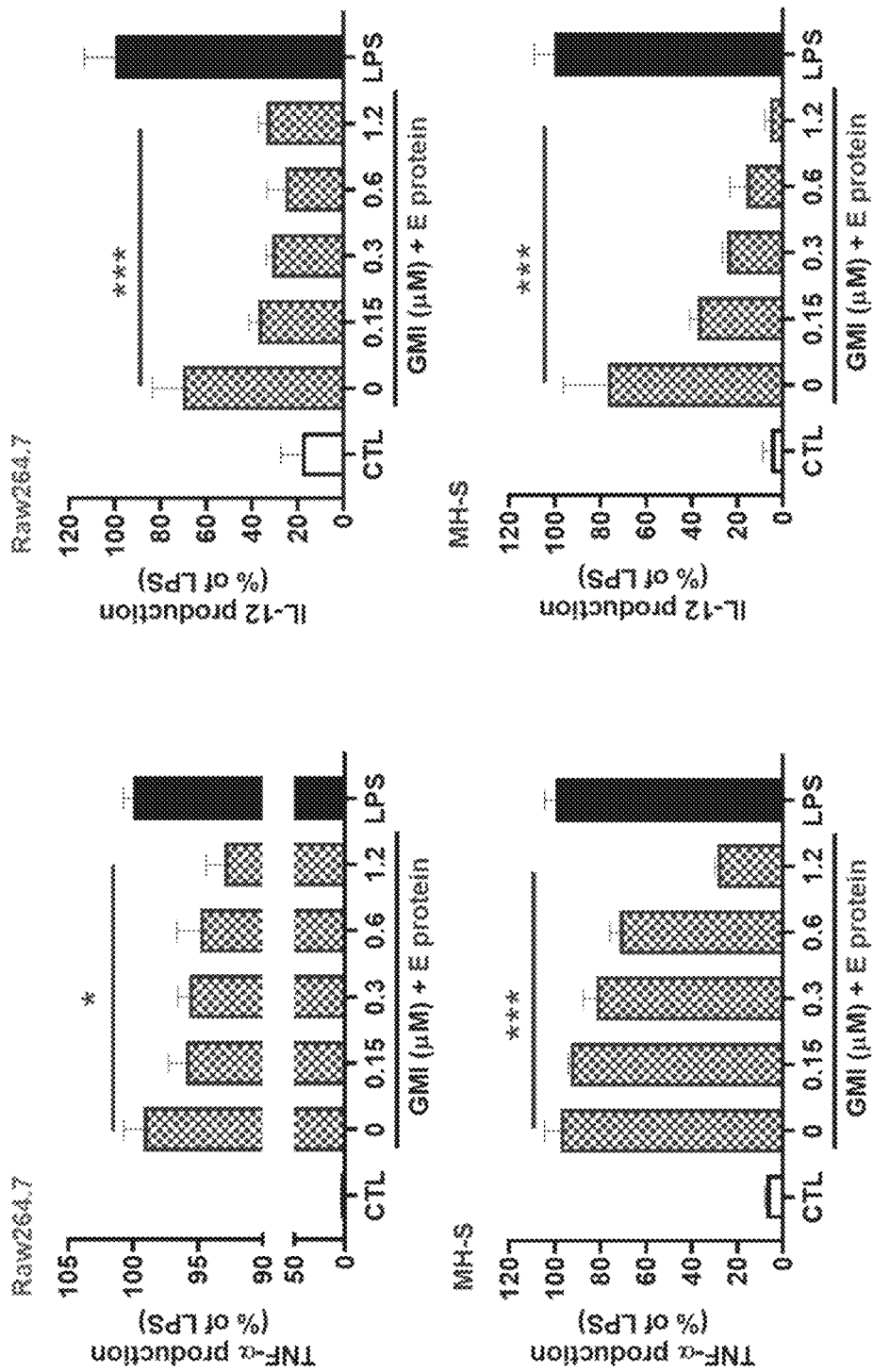

Example 3 Effects of GMI on Inhibiting SARS-CoV-2-E-Induced Inflammation of Macrophages To examine anti-SARS-CoV-2-induced cytokines effect of GMI, envelope (E) and spike(S) proteins of SARS-CoV-2 were chosen to stimulate macrophages served as an in vitro inflammatory system. As expected, GMI significantly abolished SARS-CoV-2-E-induced NO production in Raw264.7 and MH-S cells (FIG. 4A). In parallel, the levels of pro-inflammatory cytokines, including TNF-α, IL-6 and IL-12, were measured in both macrophages RAW264.7 and MH-S cells upon co-treatment of GMI and SARS-CoV-2-E. As expected, we found that GMI dramatically downregulated the secretion of SARS-CoV-2-E-induced the indicated cytokines (FIGS. 4B-D). In particular, we found that SARS-CoV-2-E exhibited the same effect on inducing inflammation of the two types of macrophages. However, GMI had a stronger anti-inflammatory effect on alveolar macrophages MH-S cells compared to Raw264.7 cells. In addition, as shown in FIGS. 5A-5D, the anti-inflammatory effect of GMI in a concentration-dependent manner (0.15 to 1.2 µM) was also observed in both Raw264.7 and MH-S cells. These findings suggest that GMI may have a better inhibitory effect on the cytokine storm caused by SARS-CoV-2 infection in lung tissue.

Figure 6A:
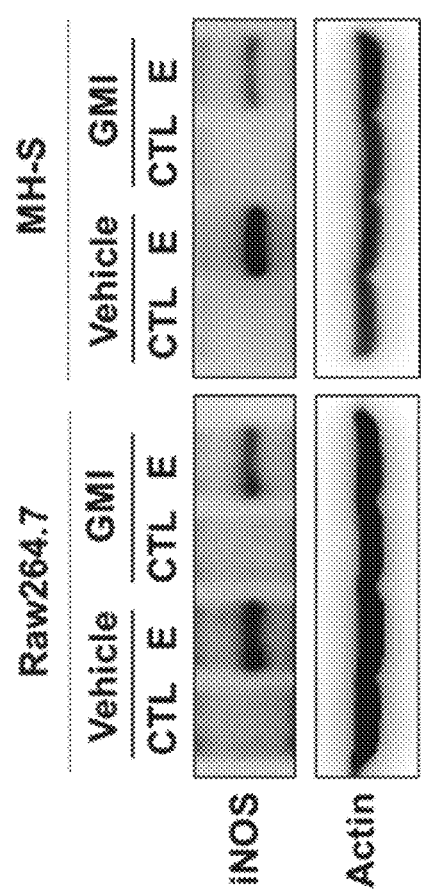
FIGS. 6A and 6B show effects of GMI on inhibiting SARS-CoV-2-E-induced iNOS and COX-2 in macrophages.
Figure 6B:
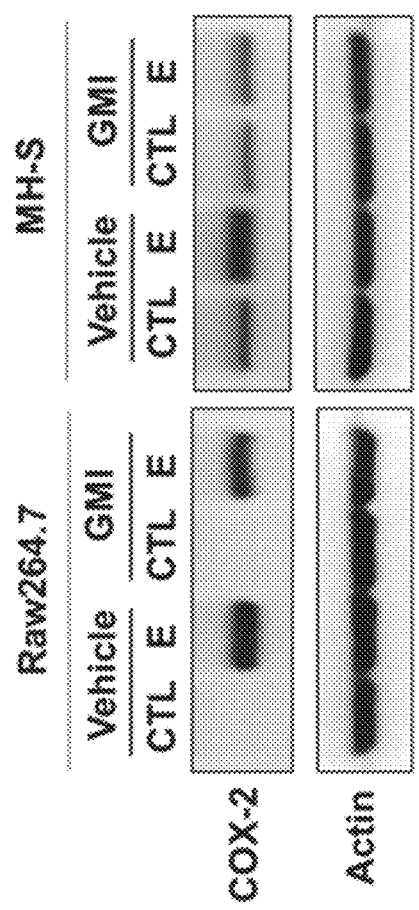

Example 4 Effects of GMI on Inhibiting SARS-CoV-2-E-Induced iNOS and COX-2 in Macrophages Similar to LPS, we found that SARS-CoV-2-E significantly induced NO production, suggesting that SARS-CoV-2-E may regulate intracellular molecules that mediate NO synthesis. Evidence shows that LPS-induced high levels of NO are mediated by inducible nitric oxide synthase (iNOS) [31]. We therefore hypothesized that SARS-CoV-2-E could up-regulate iNOS expression but GMI may abolish that of SARS-CoV-2-E stimulation. As shown in FIG. 6A, we found that GMI did not affect iNOS expression but dramatically downregulated SARS-CoV-2-E-induced levels of iNOS. Moreover, COX-2 is the enzyme largely responsible for causing inflammation [32]. We found that SARS-CoV-2-E significantly induced expression of COX-2; in contrast, GMI downregulated COX-2 levels on macrophages stimulated with SARS-CoV-2-E (FIG. 6B). These findings suggested that GMI may be a potential agent for inhibition of SARS-CoV-2-E-stimulated inflammation.

Figures 7A, 7B, 7C:
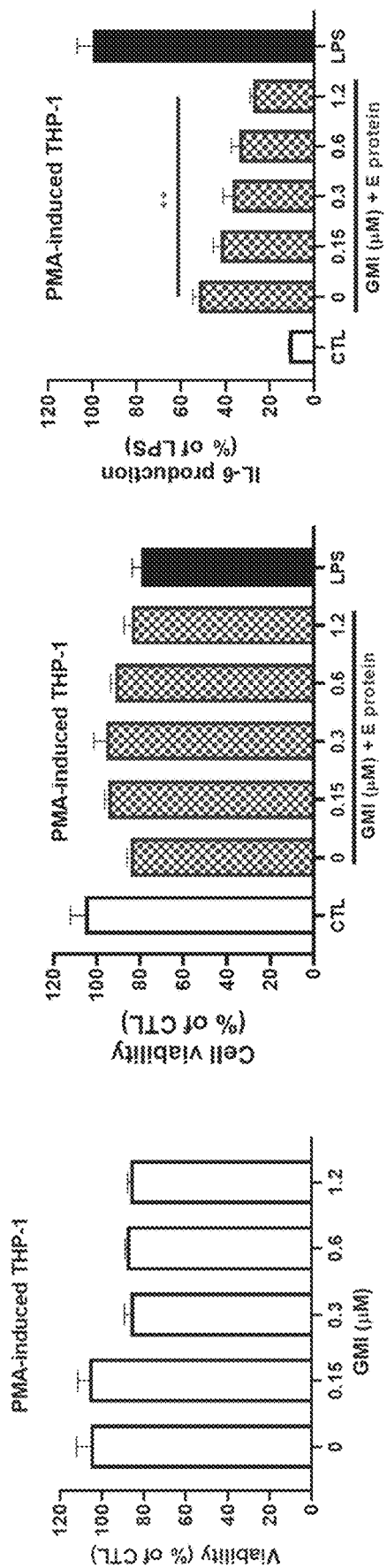
FIGS. 7A-7C show effects of GMI on viability of human macrophages and the IL-6 production in human macrophages.

Example 5 Effects of GMI on Viability of Human Macrophages and on Inhibiting SARS-CoV-2-E-Induced Inflammation in Human Macrophages To examine whether GMI exhibits cytotoxic effects on human macrophages, THP-1 cells, a type of human monocytes, were induced with phorbol 12-myristate 13-acetate (PMA; 100 ng/mL) to become human macrophages, referred hereafter as "PMA-induced THP-1 cells." Likewise, as shown in FIGS. 7A and 7B, GMI did not affect cell viability of PMA-induced THP-1 cells, at 0.15-1.2 µM, either in the presence or absence of SARS-Co-V-2 E (1 µg/mL), suggesting that GMI had no cytotoxicity for human macrophages. Furthermore, as shown in FIG. 7C, the dose-response relationship between GMI and the IL-6 production in human PMA-induced THP-1 cells was consistent with that in mouse RAW264.7 and MH-S cells as demonstrated in the aforementioned example. These findings suggested that GMI may exhibit the same anti-inflammatory effect on human macrophage as well.

Figure 8:
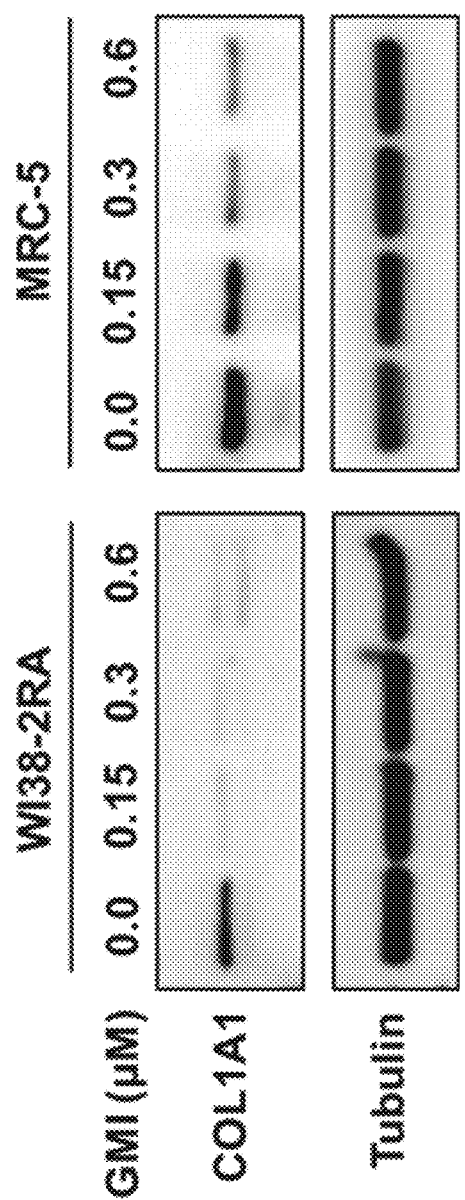
FIG. 8 shows the effect of GMI on collagen expression in the lung fibroblast WI38-2RA and MRC-5 cells. The lung fibroblast WI38-2RA and MRC-5 cells were treated with GMI (0-0.6 µM) for 48 h. The collagen I (COLA1) expression was determined by Western blot.

Example 6 Effect of GMI on Expressions of Collagen in Lung Fibroblast WI38-2RA and MRC-5 Cells Pulmonary fibrosis is a serious complication/outcome of COVID-19 pneumonia [33]. It is well-known that the alveolar epithelial cells and fibroblasts play key roles in the initiation of fibrogenesis [34]. Moreover, collagen is a specific extracellular matrix (ECM) component which contributes to fibrosis [35]. We initially examined whether GMI could mediate collagen expression in lung fibroblasts. As shown in FIG. 8, we found that GMI dramatically reduced levels of collagen I (COL1A1) in both WI38-2RA and MRC-5 cells in a concentration-dependent manner.

Example 7 Effect of GMI on Inhibiting the Cytokine Production in Blood and the Lung Tissue In Vivo To verify the in vivo anti-inflammatory effect of GMI, an inhalation method was adopted in the mice model. The scheme for the mice receiving GMI and the SARS-Co-V-2-E protein by the inhalation method is shown in detail in FIG. 9A. In particular, the mice were exposed to the SARS-Co-V-2-E protein (20 µg/mL) aerosol generated by a nebulizer. Thirty minutes after the exposure to the SARS-Co-V-2-E protein, the GMI was administered to the mice at 100 µg/mL by exposing the mice to the GMI aerosol generated by the nebulizer. The IL-6 production in the lung tissue and blood was observed either 6 hours or 24 hours after the GMI administration.

Figure 9B:
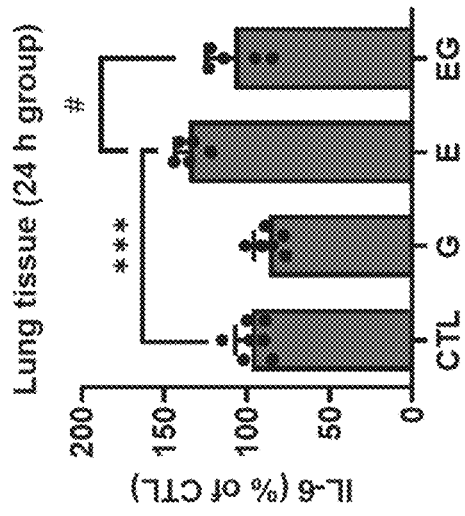
FIGS. 9A-9C show effects of GMI on the IL-6 production in vivo.
Figure 9B:
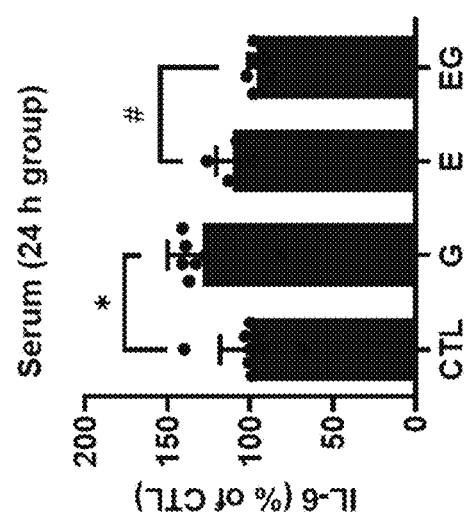
Figure 9C:
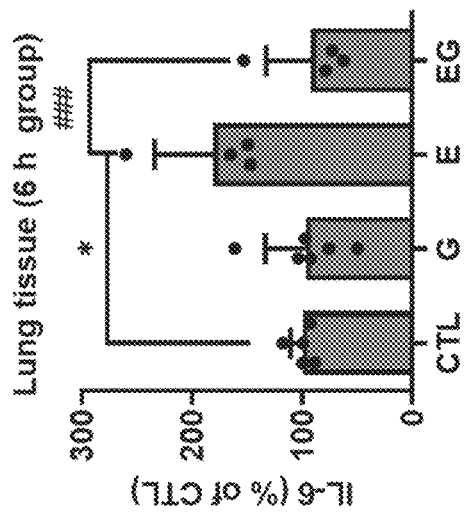
Figure 9C:
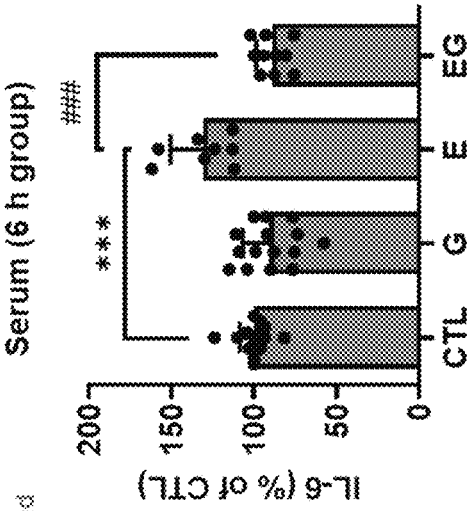
Figure 9A:
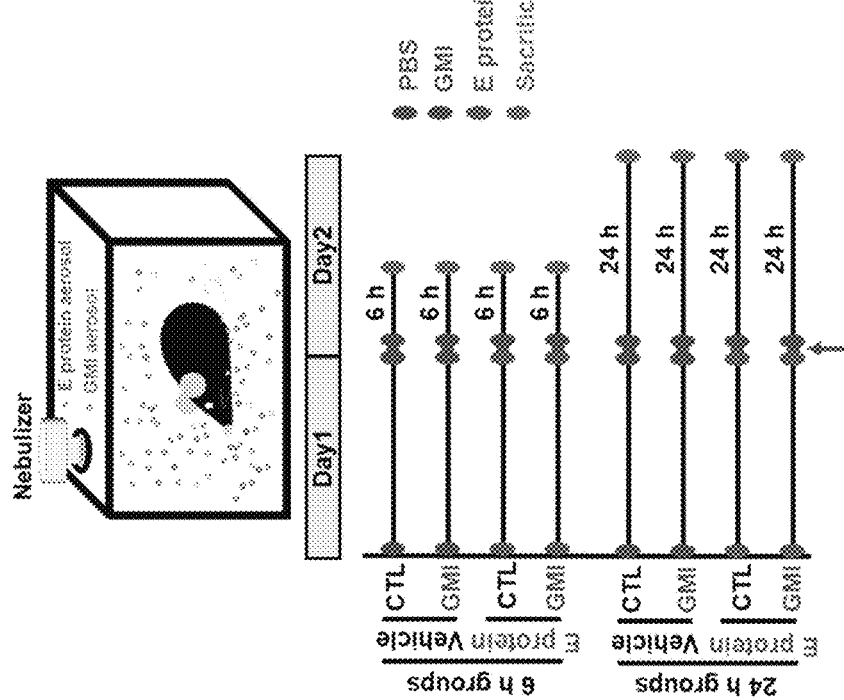

Referring to FIGS. 9B and 9C, the GMI administration following the SARS-Co-V-2-E protein exposure significantly reduced the IL-6 production both in the lung tissue (FIG. 9B) and the blood serum (FIG. 9C) of the mice. However, GMI exhibited less inhibitory effect on the IL-6 production 24 hours after the GMI administration than 6 hours after the GMI administration. These findings suggested that GMI may suppress the cytokine storm induced by the SARS-Co-V-2-E protein.

Reference

[1] M. Hoffmann, H. Kleine-Weber, S. Schroeder, N. Krüger, T. Herrler, S. Erichsen, T. S. Schiergens, G. Herrler, N. H. Wu, A. Nitsche, M. A. Müller, C. Drosten, S. Pöhlmann, SARS-CoV-2 Cell Entry Depends on ACE2 and TMPRSS2 and Is Blocked by a Clinically Proven Protease Inhibitor, Cell 181 (2) (2020) 271-280.e8.

[2] J. S. Kim, J. Y. Lee, J. W. Yang, K. H. Lee, M. Effenberger, W. Szpirt, A. Kronbichler, J. I. Shin, Immunopathogenesis and treatment of cytokine storm in COVID-19, Theranostics 11 (1) (2021) 316-329.

[3] M. Z. Tay, C. M. Poh, L. Renia, P. A. MacAry, L. F. P. Ng, The trinity of COVID-19: immunity, inflammation and intervention, Nat Rev Immunol 20 (6) (2020) 363-374.

[4] C. Wu, X. Chen, Y. Cai, J. a. Xia, X. Zhou, S. Xu, H. Huang, L. Zhang, X. Zhou, C. Du, Y. Zhang, J. Song, S. Wang, Y. Chao, Z. Yang, J. Xu, X. Zhou, D. Chen, W. Xiong, L. Xu, F. Zhou, J. Jiang, C. Bai, J. Zheng, Y. Song, Risk Factors Associated With Acute Respiratory Distress Syndrome and Death in Patients With Coronavirus Disease 2019 Pneumonia in Wuhan, China, JAMA Internal Medicine 180 (7) (2020) 934-943.

[5] M. A. Matthay, A. Leligdowicz, K. D. Liu, Biological Mechanisms of COVID-19 Acute Respiratory Distress Syndrome, Am J Respir Crit Care Med 202 (11) (2020) 1489-1491.

[6] D. C. Fajgenbaum, C. H. June, Cytokine Storm, N Engl J Med 383 (23) (2020) 2255-2273.

[7] Y. W. Zhou, Y. Xie, L. S. Tang, D. Pu, Y. J. Zhu, J. Y. Liu, X. L. Ma, Therapeutic targets and interventional strategies in COVID-19: mechanisms and clinical studies, Signal Transduct Target Ther 6 (1) (2021) 317.

[8] B. Hu, S. Huang, L. Yin, The cytokine storm and COVID-19, Journal of Medical Virology 93 (1) (2021) 250-256.

[9] Q. Ye, B. Wang, J. Mao, The pathogenesis and treatment of the 'Cytokine Storm' in COVID-19, J Infect 80 (6) (2020) 607-613.

[10] G. Cavalli, G. De Luca, C. Campochiaro, E. Della-Torre, M. Ripa, D. Canetti, C. Oltolini, B. Castiglioni, C. Tassan Din, N. Boffini, A. Tomelleri, N. Farina, A. Ruggeri, P. Rovere-Querini, G. Di Lucca, S. Martinenghi, R. Scotti, M. Tresoldi, F. Ciceri, G. Landoni, A. Zangrillo, P. Scarpellini, L. Dagna, Interleukin-1 blockade with high-dose anakinra in patients with COVID-19, acute respiratory distress syndrome, and hyperinflammation: a retrospective cohort study, Lancet Rheumatol 2 (6) (2020) e325-e331.

[11] L. Landi, C. Ravaglia, E. Russo, P. Cataleta, M. Fusari, A. Boschi, D. Giannarelli, F. Facondini, I. Valentini, I. Panzini, L. Lazzari-Agli, P. Bassi, E. Marchionni, R. Romagnoli, R. De Giovanni, M. Assirelli, F. Baldazzi, F. Pieraccini, G. Rametta, L. Rossi, L. Santini, I. Valenti, F. Cappuzzo, Blockage of interleukin-1β with canakinumab in patients with Covid-19, Scientific Reports 10 (1) (2020) 21775.

[12] F. A. Khan, I. Stewart, L. Fabbri, S. Moss, K. Robinson, A. R. Smyth, G. Jenkins, Systematic review and meta-analysis of anakinra, sarilumab, siltuximab and tocilizumab for COVID-19, Thorax 76 (9) (2021) 907-919.

[13] M. Feldmann, R. N. Maini, J. N. Woody, S. T. Holgate, G. Winter, M. Rowland, D. Richards, T. Hussell, Trials of anti-tumour necrosis factor therapy for COVID-19 are urgently needed, Lancet 395 (10234) (2020) 1407-1409.

[14] P. Richardson, I. Griffin, C. Tucker, D. Smith, O. Oechsle, A. Phelan, M. Rawling, E. Savory, J. Stebbing, Baricitinib as potential treatment for 2019-nCOV acute respiratory disease, The Lancet 395 (10223) (2020) e30-e31.

[15] A. M. Vannucchi, B. Sordi, A. Morettini, C. Nozzoli, L. Poggesi, F. Pieralli, A. Bartoloni, A. Atanasio, F. Miselli, C. Paoli, G. G. Loscocco, A. Fanelli, O. Para, A. Berni, I. Tassinari, L. Zammarchi, L. Maggi, A. Mazzoni, V. Scotti, G. Falchetti, D. Malandrino, F. Luise, G. Millotti, S. Bencini, M. Capone, M. P. Piccinni, F. Annunziato, P.

Guglielmelli, F. Mannelli, G. Coltro, D. Fantoni, M. Borella, E. Ravenda, B. Peruzzi, R. Caporale, L. Cosmi, F. Liotta, L. Lombardelli, F. Logiodice, A. Vanni, L. Salvati, C. Lazzeri, M. Bonizzoli, A. Peris, G. Cianchi, A. Bosi, M. Pucatti, P. Fontanari, S. Benemei, M. Matucci Cerinic, L. Turco, R. C. S. G. for the, Compassionate use of JAK 1/2 inhibitor ruxolitinib for severe COVID-19: a prospective observational study, Leukemia 35 (4) (2021) 1121-1133.

[16] Y. Yang, M. S. Islam, J. Wang, Y. Li, X. Chen, Traditional Chinese Medicine in the Treatment of Patients Infected with 2019-New Coronavirus (SARS-CoV-2): A Review and Perspective, Int J Biol Sci 16 (10) (2020) 1708-1717.

[17] K. Kino, A. Yamashita, K. Yamaoka, J. Watanabe, S. Tanaka, K. Ko, K. Shimizu, H. Tsunoo, Isolation and characterization of a new immunomodulatory protein, ling zhi-8 (LZ-8), from Ganoderma lucidium, J Biol Chem 264 (1) (1989) 472-8.

[18] Y. Liu, S. Bastiaan-Net, H. J. Wichers, Current Understanding of the Structure and Function of Fungal Immunomodulatory Proteins, Frontiers in Nutrition 7 (132) (2020).

[19] Q. Z. Li, Y. Z. Zheng, X. W. Zhou, Fungal immunomodulatory proteins: characteristic, potential antitumor activities and their molecular mechanisms, Drug Discov Today 24 (1) (2019) 307-314.

[20] I. L. Hsin, C. C. Ou, T. C. Wu, M. S. Jan, M. F. Wu, L. Y. Chiu, K. H. Lue, J. L. Ko, GMI, an immunomodulatory protein from Ganoderma microsporum, induces autophagy in non-small cell lung cancer cells, Autophagy 7 (8) (2011) 873-82.

[21] I. L. Hsin, C. C. Ou, M. F. Wu, M. S. Jan, Y. M. Hsiao, C. H. Lin, J. L. Ko, GMI, an Immunomodulatory Protein from Ganoderma microsporum, Potentiates Cisplatin-Induced Apoptosis via Autophagy in Lung Cancer Cells, Mol Pharm 12 (5) (2015) 1534-43.

[22] W. H. Hsu, W. L. Qiu, S. M. Tsao, A. J. Tseng, M. K. Lu, W. J. Hua, H. C. Cheng, H. Y. Hsu, T. Y. Lin, Effects of WSG, a polysaccharide from Ganoderma lucidum, on suppressing cell growth and mobility of lung cancer, Int J Biol Macromol 165 (Pt A) (2020) 1604-1613.

[23] J. Sun, X. Zhang, M. Broderick, H. Fein, Measurement of Nitric Oxide Production in Biological Systems by Using Griess Reaction Assay, Sensors 3 (8) (2003) 276-284.

[24] Z. H. Lin, J. Hu, H. Shi, C. C. Liaw, W. L. Qiu, W. H. Hsu, T. Y. Lin, Water extract of medicinal ink (WEMI) attenuates lipopolysaccharide-induced NO production of Raw264.7 cells via downregulating JAK2/STAT3-mediated iNOS expression, J Ethnopharmacol 282 (2021) 114636.

[25] T. Y. Lin, W. J. Hua, H. Yeh, A. J. Tseng, Functional proteomic analysis reveals that fungal immunomodulatory protein reduced expressions of heat shock proteins correlates to apoptosis in lung cancer cells, Phytomedicine 80 (2021) 153384.

[26] T. Y. Lin, H. Y. Hsu, Ling Zhi-8 reduces lung cancer mobility and metastasis through disruption of focal adhesion and induction of MDM2-mediated Slug degradation, Cancer Lett 375 (2) (2016) 340-8.

[27] L. Yang, X. Xie, Z. Tu, J. Fu, D. Xu, Y. Zhou, The signal pathways and treatment of cytokine storm in COVID-19, Signal Transduct Target Ther 6 (1) (2021) 255.

[28] M. Zheng, R. Karki, E. P. Williams, D. Yang, E. Fitzpatrick, P. Vogel, C. B. Jonsson, T. D. Kanneganti, TLR2 senses the SARS-CoV-2 envelope protein to produce inflammatory cytokines, Nature Immunology 22 (7) (2021) 829-838.

[29] J. Gasparello, E. D'Aversa, C. Papi, L. Gambari, B. Grigolo, M. Borgatti, A. Finotti, R. Gambari, Sulforaphane inhibits the expression of interleukin-6 and interleukin-8 induced in bronchial epithelial IB3-1 cells by exposure to the SARS-CoV-2 Spike protein, Phytomedicine 87 (2021) 153583.

[30] Y. C. Lu, W. C. Yeh, P. S. Ohashi, LPS/TLR4 signal transduction pathway, Cytokine 42 (2) (2008) 145-151.

[31] M. A. Cinelli, H. T. Do, G. P. Miley, R. B. Silverman, Inducible nitric oxide synthase: Regulation, structure, and inhibition, Med Res Rev 40 (1) (2020) 158-189.

[32] C. Chen, COX-2's new role in inflammation, Nat Chem Biol 6 (6) (2010) 401-2.

[33] S. Farooq, S. Han, S. A. Mohammad, H. Ammar, Post-COVID-19 pulmonary fibrosis, QJM 114 (9) (2021) 655-656.

[34] B. C. Willis, R. M. duBois, Z. Borok, Epithelial origin of myofibroblasts during fibrosis in the lung, Proc Am Thorac Soc 3 (4) (2006) 377-82.

[35] J. Herrera, C. A. Henke, P. B. Bitterman, Extracellular matrix as a driver of progressive fibrosis, J Clin Invest 128 (1) (2018) 45-53.

[36] J. E. Phillips, X. Zhang, J. A. Johnston, Dry powder and nebulized aerosol inhalation of pharmaceuticals delivered to mice using a nose-only exposure system, JoVE 122 (2017): e55454.

What is claimed is:

1. A method for alleviating and/or treating a SARS-CoV-2 disease in a subject in need thereof, comprising administering an effective amount of *Ganoderma* immunomodulatory protein to the subject in need thereof, wherein the *Ganoderma* immunomodulatory protein comprises the amino acid sequence of SEQ ID NO: 3.

2. The method of claim 1, wherein the *Ganoderma* immunomodulatory protein is administered at a dose of 1 μg/kg to 100 μg/kg.

3. The method of claim 2, wherein the *Ganoderma* immunomodulatory protein is administered at a dose of 2.0 μg/kg to 10 μg/kg.

4. The method of claim 1, wherein the *Ganoderma* immunomodulatory protein comprises the amino acid sequence of SEQ ID NO: 4.

5. The method of claim 1, wherein the subject is a severe COVID-19 subject.

6. The method of claim 1, further comprising administering one or more additional therapeutic agents against coronavirus.

7. The method of claim 6, wherein the one or more additional therapeutic agents is administered prior to or after administering the *Ganoderma* immunomodulatory protein or is co-administered with the *Ganoderma* immunomodulatory protein.

8. The method of claim 1, wherein the method shortens the time to recovery in subjects who were hospitalized with Covid-19, lowers respiratory tract infection, and/or reduces mortality.

9. The method of claim 1, wherein the method inhibits SARS-CoV-2-related cytokine storm and fibrosis.

10. The method of claim 1, wherein the *Ganoderma* immunomodulatory protein is administered orally or by nasal nebulization.

11. The method of claim 10, wherein the *Ganoderma* immunomodulatory protein is administered by an inhaler to the respiratory tract for local or systemic treatment of the SARS-CoV-2 coronavirus disease.

12. The method of claim 10, wherein the *Ganoderma* immunomodulatory protein is in the form of aerosol with a size of 1 μm to 10 μm.

13. A method for inhibiting SARS-CoV-2-induced inflammation in a subject in need thereof, comprising administering an effective amount of *Ganoderma* immunomodulatory protein to the subject in need thereof, wherein the *Ganoderma* immunomodulatory protein comprises the amino acid sequence of SEQ ID NO: 3.

14. The method of claim 13, wherein the inhibition of the SARS-CoV-2-induced inflammation comprises reduction in the blood NO level and/or in the level of at least one cytokine in blood and/or the lung selected from the group consisting of: IL-6, TNF-α, and IL-12.

15. The method of claim 13, wherein the method inhibits SARS-CoV-2 envelope or spike protein-induced inflammation in macrophages and/or reduces collagen in lung cells.

* * * * *

```
SEQUENCE LISTING

Sequence total quantity: 4
SEQ ID NO: 1           moltype = AA  length = 6
FEATURE                Location/Qualifiers
source                 1..6
                       mol_type = protein
                       organism = Ganoderma microsporum
SEQUENCE: 1
LAWNVK                                                                    6

SEQ ID NO: 2           moltype = AA  length = 10
FEATURE                Location/Qualifiers
source                 1..10
                       mol_type = protein
                       organism = Ganoderma microsporum
SEQUENCE: 2
DLGVRPSYAV                                                               10
```

```
SEQ ID NO: 3           moltype = AA  length = 111
FEATURE                Location/Qualifiers
source                 1..111
                       mol_type = protein
                       organism = Ganoderma microsporum
SEQUENCE: 3
MSDTALIFTL AWNVKQLAFD YTPNWGRGRP SSFIDTVTFP TVLTDKAYTY RVVVSGKDLG    60
VRPSYAVESD GSQKINFLEY NSGYGIADTN TIQVYVIDPD TGNNFIVAQW N            111

SEQ ID NO: 4           moltype = AA  length = 140
FEATURE                Location/Qualifiers
source                 1..140
                       mol_type = protein
                       organism = Ganoderma microsporum
SEQUENCE: 4
EAEAEFMSDT ALIFTLAWNV KQLAFDYTPN WGRGRPSSFI DTVTFPTVLT DKAYTYRVVV    60
SGKDLGVRPS YAVESDGSQK INFLEYNSGY GIADTNTIQV YVIDPDTGNN FIVAQWNYLE   120
QKLISEEDLN SAVDHHHHHH                                               140
```